US007605179B2

(12) United States Patent
Wischik et al.

(10) Patent No.: US 7,605,179 B2
(45) Date of Patent: Oct. 20, 2009

(54) NAPTHOQUINONE DERIVATIVES AS INHIBITORS OF TAU AGGREGATION FOR THE TREATMENT OF ALZHEIMER'S AND RELATED NEURODEGENERATIVE DISORDERS

(75) Inventors: Claude Michel Wischik, Aberdeen (GB); David Horsley, Aberdeen (GB); Janet Elizabeth Rickard, Aberdeen (GB); Charles Robert Harrington, Aberdeen (GB)

(73) Assignee: Wista Laboratories Ltd., Singapore (SG)

(*) Notice: Subject to any disclaimer, the term of this patent is extended or adjusted under 35 U.S.C. 154(b) by 642 days.

(21) Appl. No.: 10/483,266

(22) PCT Filed: Jul. 16, 2002

(86) PCT No.: PCT/GB02/03269

§ 371 (c)(1),
(2), (4) Date: Dec. 23, 2004

(87) PCT Pub. No.: WO03/007933

PCT Pub. Date: Jan. 30, 2003

(65) Prior Publication Data

US 2005/0107472 A1    May 19, 2005

(30) Foreign Application Priority Data

Jul. 16, 2001    (GB) .................................. 0117326.9

(51) Int. Cl.
*A61K 31/23*    (2006.01)
*A01N 37/00*    (2006.01)
*A01N 35/00*    (2006.01)

(52) U.S. Cl. ...................................... 514/553; 514/675
(58) Field of Classification Search ................. 514/553, 514/675
See application file for complete search history.

(56) References Cited

U.S. PATENT DOCUMENTS

| 4,897,388 | A | * | 1/1990 | Malluche ..................... 514/167 |
| 5,763,479 | A |   | 6/1998 | Chayen et al. |
| 6,953,974 | B2 |  | 10/2005 | Wischik et al. |
| 2002/0016372 | A1 | | 2/2002 | Allison |
| 2006/0014216 | A1 | | 1/2006 | Wischik et al. |

FOREIGN PATENT DOCUMENTS

| EP | 0 737 671 A2 | 10/1996 |
| JP | 8193026 | * 7/1996 |
| WO | WO 93/11231 | 6/1993 |
| WO | WO 96/04915 | 2/1996 |
| WO | WO 96/30766 | 10/1996 |
| WO | WO 01/91740 A2 | 12/2001 |
| WO | WO 02/055720 A2 | 7/2002 |
| WO | WO 02/059150 | 8/2002 |
| WO | WO 02/075318 A2 | 9/2002 |
| WO | WO 2005/030676 A1 | 4/2005 |
| WO | WO 2006/032879 A2 | 3/2006 |

OTHER PUBLICATIONS

Prophylaxis. (n.d.). Merriam-Webster's Medical Dictionary. Retrieved Dec. 21, 2007, from Dictionary.com website: http://dictionary.reference.com/browse/prophylaxis.*
Abstract, Thal, Prevention of Alzheimer disease, Alzheimer Disease and Associated Disorder, Jul.-Sep.:20(3 suppl 2):S97-9, 2006.*
Surmeir, Calcium, ageing, neuronal vulnerability in Parkinson's disease, Lancet Neurology, 6:933-38, 2007.*
Kamagai, Yoshito et al., "Inhibition of Nitric Oxide Formation by Neuronal Nitric Oxide Synthase by Quinones: Nitric Oxide Synthase as a Quinone Reductase", XP-002217439 abstract, Chemical Research in Toxicology (1998).
Danoun, Saida et al., "Synthesis and Protozoacidal Activity of New 1,4-Naphthoquinones", XP-002217440 abstract, Heterocyclic Communications: (1999).
Oommen, Elsie et al., "Antitumor Efficacy of Cyclodextrin-Complexed and Niosome-Encapsulated Plumbagin in Mice Bearing Melanoma B16F1", XP-002217441 abstract, Pharmacy and Pharmacology Communications (1999).
Bhosale, S.H., et al., "Pharmacological Studies of Isomeric [sic] Juglones on the Isolated Frog Heart", XP-002217442, Indian Journal of Pharmacology (1999).
Nishizawa Yoshinori, "Hair Growing and Restoring Agent", Patent Abstracts of Japan, 11335244, Dec. 7, 1999.
Allison, A.C., "The possible role of vitamin K deficiency in the pathogenesis of Alzheimer's disease and in augmenting brain damage associated with cardiovascular disease", XP-001117580, Medical hypothesis, vol. 57, No. 2, Aug. 2001.
Gong, C.X. et al., "Dephosphorylation of Alzheimer's disease abnormally phosphorylated tau by protein phosphatase-2A", XP-000578896, Neuroscience, vol. 61, No. 4, 1994.
Ko, Li-wen, et al., "Menadione-induced tau dephosphorylation in cultured human neuroblastoma cells", XP-001118168, Brain Research, Netherlands, Jun. 20, 1997.
U.S. Appl. No. 11/391,675, filed Mar. 29, 2006, C. M. Wischik, et al.
M. von Bergen, et al. "Assembly of tau protein into Alzheimer's paired helical filaments depends on a local sequence motif forming beta structure", Proceedings of the National Academy of Sciences of USA, National Academy of Science, May 9, 2000, vol. 97, No. 10, pp. 5129-5134.

(Continued)

Primary Examiner—Johann R Richter
Assistant Examiner—Kristie L Brooks
(74) Attorney, Agent, or Firm—Foley & Lardner LLP

(57) ABSTRACT

Provided are napthoquinone-type compounds which can be used to modulate the aggregation of protein (e.g. tau) associated with neurodegenerative disease (e.g. Alzheimer's disease). Structure-function characteristics for oxidised and reduced napthoquinone-type compounds, such as menadione-related compounds, are disclosed. The invention further provides methods of treatment or prophylaxis of neurodegenerative diseases and/or clinical dementias based on the compounds.

29 Claims, 19 Drawing Sheets

OTHER PUBLICATIONS

M. Pickhardt, et al., "Anthraquinones inhibit tau aggregation and dissolve Alzheimer paired helical filaments in vitro and in cells", Journal of Biological Chemistry, 2005, vol. 280, pp. 3628-3635.

H. Aizawa, et al., "Microtubule-binding domain of tau proteins", Journal of Biological Chemistry, 1988, vol. 263, pp. 7703-7707.

C.M. Wischik, F. Theuring and C.R. Harrington, "The molecular basis of tau protein pathology in Alzheimer's disease and related neurodegenerative dementias", In Neurobiology of Alzheimer's Disease (Eds. D. Dawbarn & S.J. Allen) Oxford University Press, Oxford, pp. 103-206.

C. Wischik, "Molecular neuropathology of Alzheimer's disease", John Libbey & Co., 1991, pp. 239-250.

R. Lai, "The Role of Abnormal Phosphorylation of Tau Protein in the Development of Neurofibrillary Pathology in Alzheimer's Disease", pp. 1-243.

C. Wischik, "Molecular Neuropathology of Alzheimer's Disease" (1989), pp. 44-70.

Garcini et al., *Biochemical and Biophysical Research Communications*, Self Assembly of Microtubule Associated Protein TAU into Filaments Resembling those found in Alzheimer Disease (1986), pp. 790-797.

Garcini et al. *J. Biocehm*. 102, No. 6, "In Vitro Conditions for the Self-Polymerization of the Microtubule-Associated Protein, Tau Factor" (1987), pp. 1415-1421.

Garcini et al., *Elsevier Science Publishers B.V.*, "Tau Factor Polymers are Similar to Paired Helical Filaments of Alzheimer's Disease" (1988), pp. 150-154.

Ksiezak-Reding and Yen, *Neuron*, vol. 6, pp. 717-728, Structural Stability of Paired Helical Filaments Requires Microtubule-Binding Domains of Tau: A Model for Self-Association (1991).

M. Goedert et al., "Tau Proteins of Alzheimer Paired Helical Filaments: Abnormal Phosphorylation of All Six Brain isoforms", *Neuron*, vol. 8, pp. 159-168, Jan. 1992.

R. Jakes et al., "Identification of 3- and 4-repeat Tau Isoforms Within The PHF in Alzheimer's Disease", *The EMBO Journal*, vol. 10, No. 10, pp. 2725-2729, 1991.

M. Novak et al., "Molecular Characterization of the Minimal Protease Resistant Tau Unit of the Alzheimer's Disease Paired Helical Filament", *The EMBO Journal*, vol. 12, No. 1, pp. 365-370, 1993.

S.-H. Yen et al., "Alzheimer's Neurofibrillary Tangles Contain Unique Epitopes and Epitopes in Common With the Heat-Stable Microtubule Associated Proteins Tau and $MAP_2$", *AJP*, Jan. 1987, vol. 126, pp. 81-91.

J.P. Brion et al., "Characterization of a Partial cDNA Specific for the High Molecular Weight Microtubule-Associated Protein MAP2 That Encodes Epitopes Shared with Paired Helical Filaments of Alzheimer's Disease", *Dementia*, 1990:1 pp. 304-315.

M.W. Klymkowsky, "Weaving a Tangled Web: the Interconnected Cytoskeleton", *Nature Cell Biology*, vol. 1, No. 5, p. E121 (1999).

Fasulo et al., "Overexpression of Alzheimer's PHF core tau fragments: implications for the tau truncation hypothesis", Rapid Science Publishers, Alzheimer's Research, vol. 2, No. 5, pp. 195-200, Oct. 1996.

Wille et al., *J. Cell Biol.*, 118 (1992) 573-584, Alzheimer-like paired helical filaments and antiparallel dimers formed from microtubule-associated protein tau in vitro.

Ksiezak-Reding and Wall, *Neurobiology of Aging*, vol. 15, No. 1, pp. 11-18. "Mass and Physical Dimensions of Two Distinct Populations of Paired Helical Filaments" (1993).

Wischik et al., *Proc. Natl. Acad. Sci. USA*, vol. 85, pp. 4506-4510 (1988) "Isolation of a fragment of tau derived from the core of the paired helical filament of Alzheimer disease".

Wischik et al., *Proc. Natl. Acad. Sci. USA*, vol. 85, pp. 4884-4888, "Structural characterization of the core of the paired helical filament of Alzheimer disease" (1988).

Ksiezak-Reding, Assembled tau filaments differ from native paired helical filaments as determiend by scanning transmission electron microscopy (STEM) (1998), pp. 86-98.

Mena et al., *Journal of Neuropathology and Experimetnal Neurology*, "A Progressive Depsotion of Paired Helical Filaments (PHF) in the Brain Characterizes the Evolution of Dementia in Alzheimer's Disease" (1991), pp. 474-490.

Mena et al., *Acta Neuropathol.*, Monitoring Pathological Assembly of tau and β-Amyloid Proteins in Alzheimer's Disease (1994), pp. 50-56.

Mena et al., *Acta Neuropathol*, "Staging the Pathological Assembly of Truncated tau Protein into Paired Helical Filaments in Alzheimer's Disease" (1995), pp. 633-641.

C.M. Wischik et al. "Quantitative Analysis of Tau Protein in Paired Helical Filament Preparations: Implications for the Role of Tau Protein Phosphorylation in PHF Assembly in Alzheimer's Disease", *Neurobiology of Aging*, vol. 16, No. 3, pp. 409-431, 1995.

C.M. Wischik et al., "Structure, Biochemistry and Molecular Pathogenesis of Paired Helical Filaments in Alzheimer's Disease", *Pathobiology of Alzheimer's Disease*, pp. 10-39, 1995.

V.M.-Y. Lee et al., "A68: A Major Subunit of Paired Helical Filaments and Derivatized Forms of Normal Tau", Science, vol. 251, pp. 675-678.

J.E. Ronden, et al. "Natural prenylquinones inhibit the enzymes of the vitamin k cycle in vitro", Biochimica et Biophysica Acta 1298, 1996, pp. 87-94.

R.K. Richards, et al., Experimental and clinical studies on the action of high doses of hykinone and other menadione derivatives Journal of Pharmacology and Experimental Therapeutics, 1945, vol. 84, pp. 93-104.

D. Vermeer, et al, "A comprehensive review of vitamin k and vitamin k antagonists", Blood Stasis and Thrombosis, Apr. 2000, vol. 14, No. 2, pp. 339-353.

J.A. Thorp, et al., "Current concepts and controversies in use of vitamin K", Drugs 49, vol. 3, pp. 377-387.

I.L. Woolf, et al, "Vitamin k and warfarin", The American Journal of Medicine, Sep. 1972, vol. 53, No. 3, pp. 261-267.

R.H. Wasserman, et al., "Metabolic roles of fat-soluble vitamins D, E and K" Annual Review of Biochemistry, 1972, vol. 41, pp. 179-202.

O. Isler, et al., "Chemistry and biochemistry of the k vitamins", Vitamins and Hormones, 1959, vol. 17, pp. 53-90.

M.J. Finkel, et al., "Vitamin k1 and the vitamin k analogues" Clinical Pharmacology & Therapeutics, 1961, vol. 3, pp. 794-814.

"Vitamin K", Goodman & Cityman, $9^{th}$ Edition, Chapter 63, pp. 1583-1590.

W. Friedrich, "Vitamins", Pub. Walter de Bruyter, Berlin, NY, 1988, pp. 286-338.

M. Nakajima, et al. "Age-dependent survival-promoting activity of vitamin k on cultured CNS neurons", Developmental Brain Research, 1993, vol. 73, pp. 17-23.

S.A.B.D. El-Fattah, et al., "The effect of dihydroxypropyl theophylline on the solubility and stability of menadione (vitamin k)", Faculty of Pharmacy, 1977, vol. 32, pp. 232-235.

N. Daabis, et al., "The influence of on-ionic surfactants on the rate of degradation of menadione (vitamin k)", Faculty of Pharmacy, pp. 750-753.

V.M. von Ardenne, et al, "Zur toxikologie des vitamin k3-natrium-bisulfit und seiner kombination mit methylenblau" Nov. 1967, pp. 1339-1346.

W. De Loecker, et al., "Effects of sodium ascorbate (vitamin c) and 2-methyle-1,4-naphthoguinone (vitamin k3) treatment on human tumor cell growth in vitro II. Synergism with combined chemotherapy action", Anticancer Research 13, 1993, pp. 103-106.

V. Noto, et al., "Effects of sodium ascorbate (vitamin c) and 2-methyle-1,4-naphthoguinone (vitamin k3) treatment on human tumor cell growth in vitro II. Synergism with combined vitamin c and k3 action", Cancer, Mar. 1989, pp. 901-906.

W.R. Leeman, et al., "Cytotoxicity of retinoic acid, menadione and aflatoxin b1 in rate liver slices using netwell inserts as a new culture system", Toxin in vitro, vol. 9, No. 3, pp. 291-298.

J. H. Chung, et al., "Metabolism and cytotoxicity of menadione and its metabolite in rate platelets", Toxicology and Applied Pharmacology, 1997, vol. 142, pp. 378-385.

T-J. Choiu, et al., "Cardiac and renal toxicity of menadione in rate" Toxicology, 1997, vol. 124, pp. 193-202.

S. Ansbacher, et al., "Toxicity of menadione, menadiol and esters", Journal of Pharmacology and Experimental Therapeutics, 1942, vol. 75, pp. 111-124.

H. Molitor, et al., "Oral and patenterial toxicity of vitamin k1, phthiocol and 2 methyl 1, 4, naphthoquinone", Proceedings of the society for Experimental Biology and Medicine 43, 1940, pp. 125-128.

R.K. Morrison, et al., "Oral toxicology studies with lapachol", Toxicology and applied Pharmacology 17, 1970, pp. 1-11.

K.V. Rao, "Quinone natural products: streptonigrin (NSC-45383) and lapachol (NSC-11905) structure activity relationships", Cancer Chemotherapy Reports Part 2, Dec. 1974, vol. 4, No. 4, pp. 11-17.

S.M. Sieber, et al., "Pharmacology of antitumor agents from higher plants", Cancer Treatment Reports, Aug. 1976, vol. 60, No. 8, pp. 1127-1139.

T.J.K. Tikkanen, et al., "Intestinal, hepatic, and circulating vitamin k levels at low and high intakes of vitamin k in rats", British Journal of Nutrition, 2000, vol. 83, pp. 185-190.

J.E. Ronden, et al., "Tissue distribution of k-vitamers under different nutritional regimens in the rat", Biochimica et Biophysica Acta 1379, 1998, pp. 16-22.

T. Tokumura, et al., "Evaluation of bioavailibility upon oral administration of phytonadione preparations in beagle dogs", Biol. Pharm. Bull. 1993, vol. 16, No. 3, pp. 319-321.

O. Y-P Hu, et al., "A pharmacokinetic study with the high-dose anticancer agent menadione in rabbits", Biopharmaceutics & Drug Disposition, 1996, vol. 17, pp. 493-499.

C. St. Grigoresco, et al., "Etude comparative de l'histopatholigie et de l'incorporation de la vitamine k-3-14C chez les rats radiosensibilises" Book reviews, pp. 505-510.

J.R. Soedirman, et al., "Pharmacokinetic and tolerance of intravenous and intramuscular phylloquinone (vitamin k1) mixed micelles formulation", British Journal of Clinical Pharmacology, 1996, vol. 41, pp. 517-523.

M.M.C.L. Groenen-van Dooren, et al., "Bioavailibility of phylloquinone and menaquinones after oral and colorectal administration in vitamin k-deficient rats", Biochemical Pharmacology, 1995, vol. 50, No. 6, pp. 797-801.

M.J. Shearer, et al, "Studies on the absorption and metabolism of phylloquinone (vitaimin k1) in man", Vitamins and Hormones, 1974, vol. 32, pp. 513-542.

D. Hollander, et al., "Colonic absorption of vitamin k-3", Journal of Laboratory Clin. Med., Apr. 1974, vol. 83, No. 4, pp. 649-656.

W. Malorni, et al., "Menadione-induced oxidative stress leads to rapid down-modulation of transferrin receptor recycling", Journal of cell Science, 1993, vol. 106, pp. 309-318.

L. Ko, et al., "Sensitization of neuronal cells of oxidative stress with mutated human α-synuclein", Journal of Neurochemistry, 2000, vol. 75, No. 6, pp. 2546-2554.

J. Markovitis, et al., "Menadione (vitamin k3) enhances the mitogenic signal of epidermal growth factor via extracellular signal-regulated kinases", International Journal of Oncology, 1998, vol. 13, pp. 1163-1170.

F.Y-H. Wu, et al., "Vitamin k3 induces cell cycle arrest and cell death by inhibiting cdc25 phosphates", European Journal of Cancer, 1999, vol. 35, No. 9, pp. 1388-1393.

J-F. Ghersi-Egea, "Electronic spin resonance detection of superoxide and hydroxyl radicals during the reductive metabolism of drugs by rat brain preparations and isolated cerebral microvessels", Free Radical Biology & Medicine, 1998, vol. 24, Nos. 7 & 8, pp. 1074-1081.

C. Vermeer, "The vitamin k-dependent carboxylation reaction", Molecular and Cellular Biochemistry, 1984, vol. 61, pp. 17-35.

C. Vermeer, "Vitamin k-dependent carboxylases from non-hepatic tissues" Febs Letter, Nov. 1982, vol. 148, No. 2, pp. 317-320.

J.W. Suttie, "Vitamin k-dependent carboxylase", Ann. Rev. Biochem., 1985, vol. 54, pp. 459-477.

C. Vermeer, "γ-carboxyglutamate-containing proteins and the vitamin k-dependent carboxylase", Biochem., J., 1990, vol. 266, pp. 625-636.

K.L. Berkner, "the vitamin k-dependent carboxylase", Recent Advances in Nutritional Sciences, Review 2000, pp. 1877-1880.

J.D. Kulman, et al., "Primary structure and tissue and distribution of two novel proline-rich γ-carboxyglutamic acid proteins", Proc. Natl. Acad. Sci. USA, 1997, vol. 94, pp. 9058-9062.

R.J.T.J. Houben, et al., "Osteocalcin binds tightly to the γ-glutamylcarboxylase at a site distinct from that of the other known vitamin k-dependnet proteims", Biochem. J., 1999, vol. 341, pp. 265-269.

R. Y. K. Lai et al., "Examination of Phosphorylated Tau Protein as PHF-Precursor at Early State Alzheimer's Disease", *Neurobiology of Aging*, vol. 16, No. 3, pp. 433-445, 1995.

C.M. Wischik, et al., "Author's response to commentaries", Neurobiology of Aging, 1995, vol. 16, No. 3, pp. 423-431.

B. H. Anderton et al., "Dendritic Changes in Alzheimer's Disease and Factors That May Underlie These Changes", *Prog. Neurobiol.*, Aug. 1998, vol. 55, No. 6, pp. 595-609.

C. Smith et al., "The molecular pathology of Alzheimer's disease: are we any closer to understanding the neurodegenerative process?", *Neuropathology and Applied Neurobiology*, vol. 20, 1994, pp. 322-338, XP002002176.

C. R. Harrington et al., "Measurement of Distinct Immunochemical Presentations of Tau Protein in Alzheimer Disease", pp. 5842-5846, Proc. Natl. Acad. Sci., vol. 88, Jul. 1991.

C.R. Harrington et al., "Competitive ELISA for the Measurement of Tau Protein in Alzheimer's Disease", pp. 261-271, Journal of Immunological Methods, 134 (1990).

Friedhoff et al., "Rapid Assembly of Alzheimer-like pared helical filaments from microtubule-associated protein tai monitored by fluorescence in solution", Biochemistry, 1995, vol. 37, pp. 10223-10230.

Friedhoff et al., "A nucleated assembly mechanism of Alzheimer paired helical filaments", Proc. Natl. Acad. Sci., USA, Dec. 1998, vol. 95, pp. 15712-15717.

Pedrotti, et al., "Interactions of microtubule-associated protein MAP2 with unpolymerized and polymerized tubulin and actin using a 96-well microtiter plate solid-phase immunoassay", Biochemistry, 1994, vol. 33, pp. 8798-8806.

Garcia de Ancos et al., "Differences in microtubule binding and self-association abilities of bovine brain tau isoforms", The Journal of Biological Chemistry, 1993, vol. 268, No. 11, pp. 7976-7982.

Wischik, Claude M., Thesis "The Structure and Biochemistry of Paired Helical Filaments in Alzheimer's Disease", Part I and II.

Wischik et al., "Subunit Structure of Paired Helical Filaments in Alzheimer's Disease", 1985, vol. 100, pp. 1905-1913.

\* cited by examiner

KI (nM)   B$_{50}$ (μM)
II
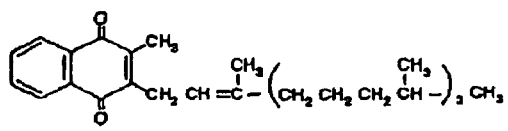
K$_1$              1605        59.83
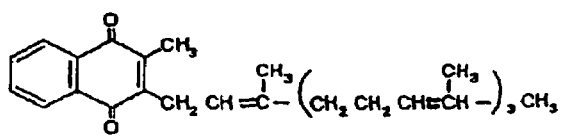
K$_2$              1540        33.46
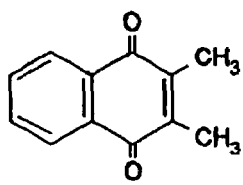
DH10               221         4.80
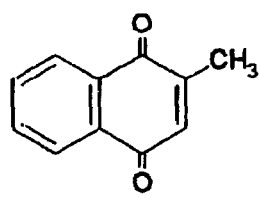
K$_3$              128         2.78
Figure 2a KI (nM)   B$_{50}$ (μM)
III
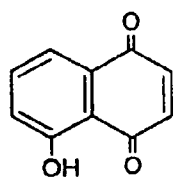
DH14 — —
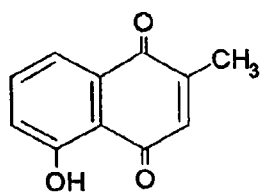
DH2   131   2.85
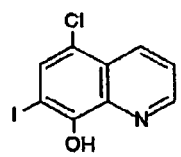
DH16 — —
Figure 2b KI (nM)   B $_{50}$ (µM)
IV
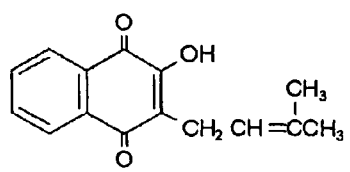
DH1    513    11.14
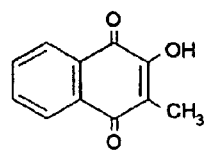
DH15   —    —
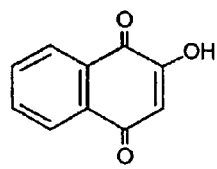
DH7    —    —
Figure 2c

|  | KI (nM) | B$_{50}$ (μM) |
|---|---|---|
| V 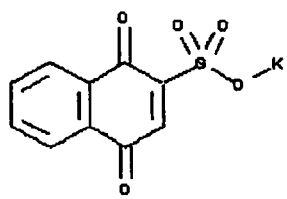 DH8 | 157 | 3.41 |
| 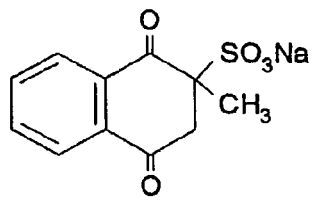 DH3 | 630 | 13.68 |
| 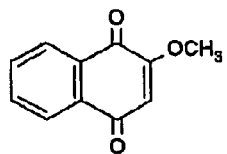 DH17 | 293 | 6.4 |
| 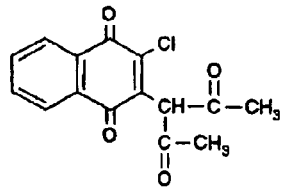 DH19 | — | — |
Figure 2d

| | KI (nM) | B$_{50}$ (μM) |
|---|---|---|
| VI | | |
| 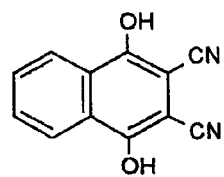 DH4 | — | — |
| 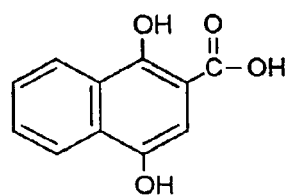 DH5 | 118 | 2.56 |
Figure 2e KI (nM) B$_{50}$ (μM)
VII
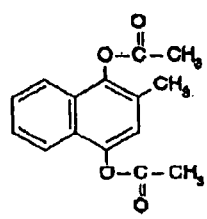
DH9  127  2.76
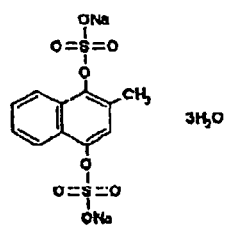
DH13  263  5.71
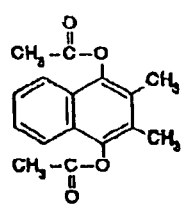
DH11  674  14.62
Figure 2f

| | | KI (nM) | B$_{50}$ (μM) |
|---|---|---|---|
| VIII | | | |
| 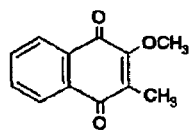 | DH18 | | 35 |
| 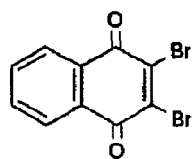 | DH20 | — | — |
Figure 2g

*Inhibition of production of 25 kD band (K25)
from full-length tau (T40)
in the presence of Vitamin K3*

*Production of 25 kD band:*

No K3                      *22% of T40*
1-2 μM K3            *5% of T40*

*p = 0.0015*

Inhibition of production of 25 kD band (K25) from K40 tau fragment (SS190-441) in the presence of Vitamin K3

*Production of 25 kD band:*

| | |
|---|---|
| No K3 | 59% of K40 |
| 1-2 µM K3 | 31% of K40 |

$p = 0.0012$

Diseases of protein aggregation

| Protein | Disease | Aggregating domain and/or mutations | Fibril subunit size (kDa) | Reference |
|---|---|---|---|---|
| *Neurodegenerative disorders* | | | | |
| Prion protein | Prion diseases (CJD, nvCJD, Fatal familial Insomnia, Gerstmann-Straussler-Scheinker syndrome, Kuru) | *Inherited and sporadic forms* PrP-27-30; many mutations Fibrillogenic domains: 113-120, 178-191, 202-218 | 27 | Prusiner (1998) Gasset et al. (1992) |
| Tau protein | Alzheimer's disease, Down's syndrome, FTDP-17, CBD, post-encephalitic parkinsonism, Pick's disease, parkinsonism with dementia complex of Guam | *Inherited and sporadic forms* Truncated tau (tubulin-binding domain) 297-391 Mutations in tau in FTDP-17 Many mutations in presenilin proteins | 10-12 | Wischik et al. (1988) Hutton et al. (1998) Czech et al. (2000) |
| Amyloid β-protein | Alzheimer's disease, Down's syndrome | *Inherited and sporadic forms* Amyloid β-protein; 1-42(3); 11 mutations in APP in rare families | 4 | Glenner & Wong. (1984) Goate et al. (1991) |
| Huntingtin Ataxins (1, 2, 3, 7) Atrophin Androgen receptor | Huntington's disease Spinocerebellar ataxias (SCA1, 2, 3, 7) Dentatorubropallidoluysian atrophy (DRPLA) Spinal and bulbar muscular atrophy | N-termini of protein with expanded glutamine repeats Proteins with expanded glutamine repeats Proteins with expanded glutamine repeats Proteins with expanded glutamine repeats | 40 | DiFiglia et al. (1997) Paulson et al. (1999) Paulson et al. (1999) Paulson et al. (1999) |
| Neuroserpin | Familial encephalopathy with neuronal inclusion bodies (FENIB) | Neuroserpin; S49P, S52R | 57 | Davis et al. (1999) |
| α-Synuclein | Parkinson's disease, dementia with Lewy bodies, multiple system atrophy | *Inherited and sporadic forms* A53T, A30P in rare autosomal-dominant PD families | 19 | Spillantini et al. (1998) Polymeropoulos et al. (1997) |
| Cystatin C | Hereditary cerebral angiopathy (Icelandic) | Cystatin C less 10 residues; L68Q | 12-13 | Abrahamson et al. (1992) |
| Superoxide dismutase 1 | Amyotrophic lateral sclerosis | SOD1 mutations | | Shibata et al. (1996) |
| *Non-neurodegenerative disorders* | | | | |
| Haemoglobin | Sickle cell anaemia Inclusion body haemolysis | Haemoglobin beta chain (S) Many mutations | | Carrell & Gooptu (1998) |
| Serpins | α1-Antitrypsin deficiency (emphysema, cirrhosis) Antithrombin deficiency (thromboembolic disease) C1-inhibitor deficiency (angioedema) | Mutations Mutations Mutations | | Lomas et al. (1992) Carrell & Gooptu (1998) Carrell & Gooptu (1998) |
| Immunoglobulin light chain | Plasma cell dyscrasias (primary systemic AL amyloidosis) | light chain or fragments | 0.5-25 | Westermark et al. (1985) |
| Serum amyloid A | Reactive, secondary systemic AA amyloidosis Chronic inflammatory disease | 76-residue fragment (critical residues 2-12) | 4.5-7.5 | Westermark et al. (1985) |

Figure 4

| Protein | Disease | Details | | Reference |
|---|---|---|---|---|
| Transthyretin | Familial amyloid polyneuropathy (systemic; FAP I) | Tetramer dissociated to conformational monomer variant. Many mutations (some not associated with amyloid; several different types of disease) | 10-14 | Gustavsson et al. (1991) |
| | Senile cardiac amyloidosis | Normal transthyretin | 10-14 | Gustavsson et al. (1991) |
| Gelsolin | Familial amyloidosis - Finnish type (FAP IV) | D187Q leads to truncated 173-225/243 (critical residues 182-192) | 9.5 | Maury & Baumann (1990) |
| β2-Microglobulin | Haemodialysis amyloidosis<br>Prostatic amyloid | β2-Microglobulin | 12-25 | Gorevic et al. (1985) |
| Apolipoprotein AI | Familial amyloid polyneuropathy (systemic; FAP III) | N-terminal 83-93 residues; G26R, W50R, L60R | 9 | Booth et al. (1997) |
| Lysozyme | Familial visceral amyloidosis | Lysozyme or fragments (with or without I56T, D67H) | 14 | Pepys et al. (1993) |
| Amylin (Islet amyloid polypeptide) | Type II diabetes (NIDDM) | Fragments (critical core of 20-29); no mutations | 3.9 | Westermark (1990) |
| Fibrinogen α-chain | Hereditary renal amyloidosis | Fibrinogen fragments | 7-10 | Uemichi et al. (1992) |
| Procalcitonin | Medullary carcinoma of thyroid | Calcitonin fragments | 3.4 | Sletten et al. (1976) |
| Atrial natriuretic factor | Cardiac amyloidosis | ANF, no mutants | 3.5 | Johansson et al. (1987) |
| Insulin | Injection localised amyloidosis | Insulin | | Dische et al. (1988) |
| Other proteins forming amyloid | (in vitro) | Other proteins | | Chiti et al. (1999) |

Figure 4 Cont ...

Proto-assembly of tau

Truncation of N- and C-terminal domains

Minimal core tau unit dimer

Further binding of tau

Further truncation

Building up of core PHF

Vitamin K3 : 12 kD model
↑T40 + 12 kD ⇒ ↑12 kD cell assay

Cellular activity predicted via standard inhibition model:

acitivity = [ tau ] / ([ tau ] + Kd * ( 1 + [ VK3 ] / KI ))

| | |
|---|---|
| Observed vs predicted activity | r = 0.925 |
| Intracellular tau concentration | 500 nM |
| Tau-tau binding affinity | 22 nM |
| Vitamin K3 KI | 128 nM |

DH9 : 12 kD model
↑T40 + 12 kD ⇒ ↑12 kD cell assay

Cellular activity predicted via standard inhibition model:

acitivity = [ tau ] / ([ tau ] + Kd * ( 1 + [ DH9 ] / KI ))

| | |
|---|---|
| Observed vs predicted activity | r = 0.988 |
| Intracellular tau concentration | 500 nM |
| Tau-tau binding affinity | 22 nM |
| DH9 KI | 127 nM |

DH17 : 12kD model
↑T40 + 12 kD ⇒ ↑ 12kD

Cellular activity predicted via standard inhibition model:

activity = [tau]/([tau]+Kd*(1+[DH17]/Ki))

| | |
|---|---|
| Observed vs predicted activity | r=0.808 |
| Intacellular tau concentration | 500nM |
| Tau-tau binding affinity | 22nM |
| DH17 Ki | 293nM |

NAPTHOQUINONE DERIVATIVES AS INHIBITORS OF TAU AGGREGATION FOR THE TREATMENT OF ALZHEIMER'S AND RELATED NEURODEGENERATIVE DISORDERS

This application is the National Phase Application of International Application PCT/GB02/03269 filed on Jul. 16. 2002.

TECHNICAL FIELD

The present invention generally concerns the aggregation of proteins associated with neurodegenerative disease such as Alzheimer's disease (AD) and compounds capable of modulating such aggregation.

BACKGROUND TO INVENTION

Conditions of dementia such as AD are frequently characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (Mukaetova-Ladinska, E. B. et al. (2000) Am. J. Pathol. Vol. 157, No. 2, 623-636).

In AD, both neuritic plaques and NFTs contain paired helical filaments (PHFs), of which a major constituent is the microtubule-associated protein tau (Wischik et al. (1988a) PNAS USA 85, 4506-4510). Plaques also contain extracellular β-amyloid fibrils derived from the abnormal processing of amyloid precursor protein (APP; Kang et al. (1987) Nature 325, 733). An article by Wischik et al. (in 'Neurobiology of Alzheimer's Disease', 2nd Edition (2000) Eds. Dawbarn, D. and Allen, S. J., The Molecular and Cellular Neurobiology Series, Bios Scientific Publishers, Oxford) discusses in detail the putative role of tau protein in the pathogenesis of neurodegenerative dementias. Loss of the normal form of tau, accumulation of pathological PHFs and loss of synapses in the mid-frontal cortex all correlate with associated cognitive impairment. Furthermore, loss of synapses and loss of pyramidal cells both correlate with morphometric measures of tau-reactive neurofibrillary pathology, which parallels, at a molecular level, an almost total redistribution of the tau protein pool from a soluble to a polymerised form (i.e. PHFs) in Alzheimer's disease.

Tau exists in alternatively-spliced isoforms, which contain three or four copies of a repeat sequence corresponding to the microtubule-binding domain (Goedert, M., et al. (1989) EMBO J. 8, 393-399; Goedert, M., et al. (1989) Neuron 3, 519-526). Tau in PHFs is proteolytically processed to a core domain (Wischik, C. M., et al. (1988b) PNAS. USA 85, 4884-4888; Wischik et al. (1988a) Loc cit.); Novak, M., et al. (1993) EMBO J. 12, 365-370) which is composed of a phase-shifted version of the repeat domain; only three repeats are involved in the stable tau-tau interaction (Jakes, R., et al. (1991) EMBO J. 10, 2725-2729). Once formed, PHF-like tau aggregates act as seeds for the further capture and provide a template for proteolytic processing of full-length tau protein (Wischik et al. 1996 Proc Natl Acad Sci USA 93, 11213-11218).

The phase shift which is observed in the repeat domain of tau incorporated into PHFs suggests that the repeat domain undergoes an induced conformational change during incorporation into the filament. During the onset of AD, it is envisaged that this conformational change could be initiated by the binding of tau to a pathological substrate, such as damaged or mutated membrane proteins (see Wischik, C. M., et al. (1997) in "Microtubule-associated proteins: modifications in disease", eds. Avila, J., Brandt, R. and Kosik, K. S. (Harwood Academic Publishers, Amsterdam) pp. 185-241).

In the course of their formation and accumulation, PHFs first assemble to form amorphous aggregates within the cytoplasm, probably from early tau oligomers which become truncated prior to, or in the course of, PHF assembly (Mena, R., et al. (1995) Acta Neuropathol. 89, 50-56; Mena, R., et al. (1996) Acta Neuropathol. 91, 633-641). These filaments then go on to form classical intracellular NFTs. In this state, the PHFs consist of a core of truncated tau and a fuzzy outer coat containing full-length tau (Wischik., C. M., et al, (1996) loc. cit.). The assembly process is exponential, consuming the cellular pool of normal functional tau and inducing new tau synthesis to make up the deficit (Lai, R. Y. K., et al., (1995), Neurobiology of Ageing, Vol. 16, No. 3, 433-445). Eventually, functional impairment of the neurone progresses to the point of cell death, leaving behind an extracellular NFT. Cell death is highly correlated with the number of extracellular NFTs (Wischik et al. 2000, loc.cit). As tangles are extruded into the extracellular space, there is progressive loss of the fuzzy outer coat of the neurone with corresponding loss of N-terminal tau immunoreactivity, but preservation of tau immunoreactivity associated with the PHF core (Bondareff, W. et al., (1994) J. Neuropath. Exper. Neurol., Vol. 53, No. 2, 158-164).

Clearly the identification of compounds that could modulate the aggregation of disease-associated proteins such as tau is of great interest.

WO 96/30766 (F Hoffman-La Roche) discloses assays for the inhibition of tau-tau association, and certain inhibitors identified using the assays. FIGS. 23 and 24 therein rank certain compounds according to their inhibitory properties. Vitamin K (=K2) has a value of 0.674 and menadione (also known as Vitamin K3) is denoted as having a value of 1.042. In the ranking a value of 1 represents binding equivalent to that observed in the absence of compound.

Of course, vitamin K is well known, per se, as a therapeutic. A brief overview of Vitamin K is given in "Goodman and Gilman's The Pharmacological Basis of Therapeutics", 9th edition, pp 1582-1585, 1998. More comprehensive reviews are provided in William Friedrich, "Vitamins", pp 285-338, 1988; Thorp et al (1995), Drugs 49, 376-387; Vermeer and Schurgers (2000), Blood Stasis and Thrombosis, 14, 339-353. The reduced form of vitamin K acts as a cofactor for the enzyme gamma-glutamyl carboxylase. This enzyme is responsible for the conversion of glutamic acid residues to gamma-carboxyglutamate on the vitamin K—dependent clotting factors (factors II, VII, IX, X and the anticoagulation proteins, protein C and protein S). Other gamma-carboxyglutamic acid containing proteins (so called Gla-proteins) have been found in plasma (protein Z), bone (osteocalcin), kidney, lung and testicular tissue. The functions of non-haematological Gla-proteins are outlined in Vermeer and Schurgers (2000, loc cit.). However such proteins are not found in the brain (Vermeer (1990), Biochem J, 266, 625-636).

Traditional therapeutic uses of Vitamin K analogues include hypoprothrominaemia in adults and the newborn, inadequate absorption of lipid-soluble substances, and intestinal malabsorbtion syndromes such as cystic fibrosis, sprue, Crohn's disease and enterocolitis.

In addition to the therapeutic uses described above, vitamin K3 is also known to have anti-tumour activity in vitro against a broad range of rodent and human tumour cell lines (Hu et al., 1996). The mechanism of this activity is not known. It has been shown that vitamin K3 has complex effects on several second messenger kinase cascades (Markovits et al., 1998;

Wu and Sun 1999), and it has been proposed specifically that vitamin K3 forms a covalent bond with kinases/phsophatases containing the peptide sequence (I/V)HCXXXXXR(S/T)G inducing cell-cycle arrest and cell death by inhibitng Cdc25 phosphatase. However the consensus sequence [HCXXXXXR(S/T)G] is not found in the repeat domain of tau.

One study (Nakajima et al., 1993) examined the effects of vitamin K derivatives on cultured CNS neurones and found that vitamins K1 and K2 had prominent survival promoting effects in the range 10 nM—1 μM. By contrast, vitamin K3 (menadione) had only ~10% of this survival promoting activity, and this only at 1 μM. Whatever the mechanism of this effect, it was not dependent on the vitamin K cycle, since coumarin anticoagulant which interferes with epoxide reductase step had no effect on the survival promotion assay. Using cultured human neuroblastoma cells, Ko et al. (1997) showed that menadione at high doses (200 μM) caused both prominent dephosphorylation of tau protein, and oxidation of a broad range of proteins. Interestingly, for the reasons discussed in detail in Wischik et al. (2000), tau protein dephosphorylation might be expected to enhance tau protein aggregation.

More recently, Ko et al. (2000) discusses the role of pathogenic mutations in alpha-synuclein in sensitising neuronal cells to oxidative stress induced by high dose menadione. In this paper, the authors argue that thiol-depletion induced by compounds which generate oxidative-stress is a general mechanism responsible for toxicity of mutant alpha-synuclein in hereditary Parkinson's disease, with the implication that rational approaches to therapy would be based on counteracting the oxidant damage produced by substances such as menadione.

However, apart from the isolated data given in WO 96/30766 (F Hoffman-La Roche), no investigation has been carried out to demonstrate and optimise a role for napthoquinone-type compounds in the inhibition of aggregation of protein associated with neurodegenerative disease.

DISCLOSURE OF THE INVENTION

The present inventors have investigated the structures of napthoquinone-type compounds which can be used to inhibit the aggregation of protein associated with neurodegenerative disease. Using novel assay technology they have demonstrated that, contrary to the data given in WO 96/30766, menadione and related compounds may be highly effective inhibitors. Detailed structure-function characteristics for napthoquinone-type compounds, such as Vitamin K-derived compounds, have been determined in respect of their use as protein (e.g. tau protein) aggregation inhibitors. As will be appreciated by those skilled in the art, in the light of the present disclosure, these results demonstrate utility for such compounds inter alia in the treatment of diseases (such as AD) associated with such protein aggregation.

More specifically, the inventors have determined that it may be advantageous for potency that the '3' position group, generally substituent $R^{2A}$ in the structural formulae below, be absent or relatively short (e.g. as in menadione) rather than an extended group (e.g. as in Vitamin K2 or K3). This is not only unexpected in the light of WO 96/30766, but also in the light of earlier more general structure function relationships for these compounds. For example in: Isler and Wiss (1959), Vitamins and Hormones, 17, 53-90, at page 77, the "biological activity" of Vitamin K1 and K2, and their analogs, is shown to decrease as the '3' position side chain is shortened.

Compounds of the Invention

Aspects of the present invention are based on uses of Vitamin K-type compounds having relatively short groups, or no group, at the 3' position (as defined in more detail below) in relation to neurodegenerative diseases of protein aggregation.

As described above, the class of compounds known as "Vitamin K" correspond in their naturally occurring forms to a dietary principle essential for the normal biosynthesis of several factors required for the clotting of blood. This activity is associated with at least two distinct naturally occurring substances, designated vitamin K1 (phytonadione, or 2-methyl-3-phytyl-1,4-naphthoquinone, the form occurring in leafy vegetables) and vitamin K2 (menaquinone). The latter represent a series of compounds (the menaquinones) in which the phytyl side chain of phytonadione is replaced by a side chain built of 2 to 13 prenyl units, and numbered accordingly. Intestinal bacteria and liver are able synthesise menaquinones (predominantly manaquinone-4) from the synthetic lipid-soluble analogue menadione. Menadione has 2 common water-soluble derivatives, menadiol sodium phosphate and menadione sodium bisulphate which are converted to menadione after administration. Other compounds related to menadione have been investigated for anti-tumour activity, in particular compounds related to lapachol (2 hydroxy-3-(3-methyl-2-butenyl)-1,4-naphthoquinone). Structural variants in the side-chain at position 3 are reviewed by Rao (1974). Some typical toxicological and clinical data for lapachol are provided by Seiber et al. (1976) and Morrison et al. (1970).

The invention particularly pertains to compounds of the following formula:

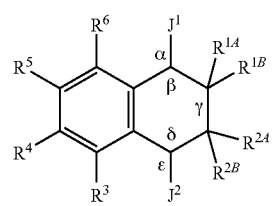

I wherein:

$J^1$ and $J^2$ are both =O; i.e. the covalent bonds marked α and ε are double bonds; β and δ are single bonds, and the covalent bond marked γ is a double bond with $R^{1B}$ and $R^{2B}$ both absent;

or the covalent bond marked γ is a single bond.

In another embodiment:

$J^1$ is —$OR^7$ and $J^2$ is —$OR^8$; i.e. the covalent bonds marked α and ε are single bonds; β and δ are double bonds, and the covalent bond marked γ is a single bond with $R^{1B}$ and $R^{2B}$ both absent.

Both oxidised and reduced forms of the compounds described herein may be used in the present invention.

Thus in particular embodiments, the compounds have the following formula:

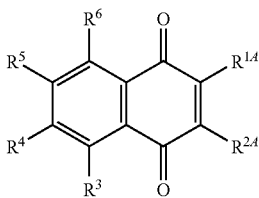

II

In one embodiment, the compounds have the following formula:

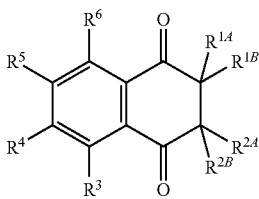

III

In one embodiment, the compounds have the following formula:

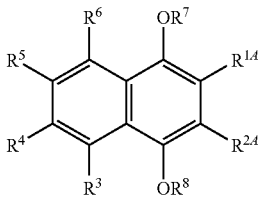

IV

Various preferred, specific, embodiments are shown in FIG. 2 with Vitamin K1 and K2, and certain other inactive compounds not forming part of the present invention, being included for comparison.

$R^{2A}$ and $R^{2B}$ if present

Compounds of the invention are those in which $R^{2A}$ is a relatively short group (compare K1 and K2 with DH10 and K3 for example).

Thus $R^{2A}$ may be independently selected from —H, $C_{1-7}$alkyl (including, e.g. unsubstituted $C_{1-7}$alkyl, substituted $C_{1-7}$alkyl such as $C_{1-7}$haloalkyl, $C_{1-7}$hydroxyalkyl, $C_{1-7}$aminoalkyl, $C_{1-7}$carboxyalkyl etc.), —OH, $C_{1-7}$alkoxy, acyloxy, —COOH, ester, —SO$_3$H, —SO$_3$M, sulfonate, $C_{1-7}$alkylsulfonate, or a "short chain alkyl group" by which is meant linear or branched alkyl group having from 1-15 carbon atoms, most preferably 1-12, more preferably 1-10, e.g. 1, 2, 3, 4, 5, 6, 7, 8, 9, or 10 carbon atoms, which may be saturated or partially unsaturated.

The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group." Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

In one embodiment, the short chain alkyl group is one of the following groups, wherein n is 0, 1, or 2:

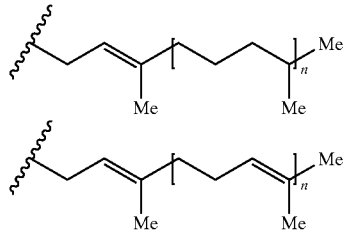

$R^{2B}$ if present will be selected from the same groups as $R^{2A}$, and may be the same or different to $R^{2A}$. However preferred compounds are those in which $R^{2B}$ is absent.

$R^{1A}$, $R^{1B}$

Each of $R^{1A}$, $R^{1B}$ is independently —H, $C_{1-7}$alkyl (including, e.g. unsubstituted $C_{1-7}$alkyl, substituted $C_{1-7}$alkyl such as $C_{1-7}$haloalkyl, $C_{1-7}$hydroxyalkyl, $C_{1-7}$aminoalkyl, $C_{1-7}$carboxyalkyl etc.), —OH, $C_{1-7}$alkoxy, acyloxy, —COOH, ester, —SO$_3$H, —SO$_3$M, sulfonate, $C_{1-7}$alkylsulfonate, or a short chain alkyl group.

M denotes a cation or cations of charge or cumulative charge to counter the charge on the —SO$_3^-$ group. In one embodiment, M denotes an alkali ion, such as Li$^+$, Na$^+$, K$^+$, or Cs$^+$, more preferably Na$^+$ or K$^+$.

Preferred compounds are those in which $R^{1B}$ is absent, although compounds in which it is not absent (such as DH3 for example) do show activity.

Preferred compounds are those in which $R^{1A}$ is alkyl, such as methyl (compare DH2 and DH14 for example, also DH1, DH7 and DH15). However other small groups in place of methyl, such as a sulphate group, may also be preferred (compare K3 and DH8). Preferably the $R^{1A}$ group is an electron donating group.

$R^{1A}$, $R^{1B}$, $R^{2A}$, $R^{2B}$

In one embodiment, each of $R^{1A}$, $R^{1B}$, $R^{2A}$, $R^{2B}$ is independently —H; -Me, -Et, -nPr, -iPr, -nBu, -sBu, -iBu, -tBu; —OH; —OMe, —OEt, —O(nPr), —O(iPr), —O(nBu), —O(sBu), —O(iBu), —O(tBu); —OC(=O)Me, —OC(=O)Et, —OC(=O)(nPr), —OC(=O)(iPr), —OC(=O)(nBu), —OC(=O)(sBu), —OC(=O)(iBu), or —O(C=O)(tBu); —C(=O)OMe, —C(=O)OEt, —C(=O)O(nPr), —C(=O)O(iPr), —C(=O)O(nBu), —C(=O)O(sBu), —C(=O)O(iBu), —C(=O)O(tBu); —SO$_3$H, —SO$_3$M, —SO$_3$Me, —SO$_3$Et, —SO$_3$(nPr), —SO$_3$(iPr), —SO$_3$(nBu), —SO$_3$(sBu), —SO$_3$(iBu), —SO$_3$(tBu).

In one embodiment, each of $R^{1A}$, $R^{1B}$, $R^{2A}$, $R^{2B}$ is independently —H, -Me, -Et, —OMe, —OEt, —OH, —OMe, —OEt, —OC(=O)Me, —OC(=O)Et, —COOH, —COOMe, —COOEt, —SO$_3$H, —SO$_3$M, —SO$_3$Me, —SO$_3$Et, or —CH$_2$CH=C(CH$_3$)$_2$.

In one embodiment, each of $R^{1A}$, $R^{1B}$, $R^{2A}$, $R^{2B}$ is independently —H, -Me, —OMe, —OH, —OMe, —OC(=O)Me, —COOH, —COOMe, —SO$_3$H, —SO$_3$M, —SO$_3$Me, or —CH$_2$CH=C(CH$_3$)$_2$.

In one embodiment, $R^{1A}$ is -Me, and $R^{1B}$ and $R^{2B}$ are absent:

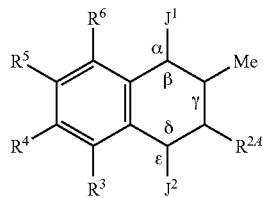

V

In one embodiment, $R^{1A}$ and $R^{1B}$ are both —H, and $R^{2b}$ and $R^{2B}$ are as defined above:

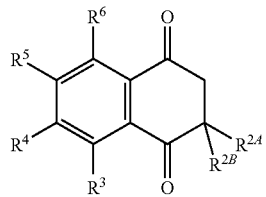

VI

In one embodiment, $R^{2A}$ and $R^{2B}$ are both —H, and $R^{1A}$ and $R^{1B}$ are as defined above:

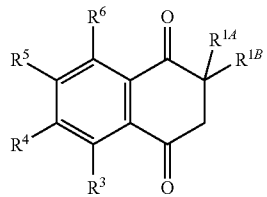

VII

In one embodiment, $R^{1B}$ and $R^{2B}$ are both —H, and $R^{1B}$ and $R^{2B}$ are as defined above:

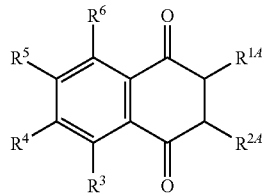

VIII $R^3$, $R^4$, $R^5$, and $R^6$

Each of $R^3$, $R^4$, $R^5$, and $R^6$ is independently —H, —OH, C$_{1-7}$alkyl (including, e.g. unsubstituted C$_{1-7}$alkyl, substituted C$_{1-7}$alkyl such as C$_{1-7}$haloalkyl, C$_{1-7}$hydroxyalkyl, C$_{1-7}$aminoalkyl, C$_{1-7}$carboxyalkyl etc.), C$_{1-7}$alkoxy, or acyloxy.

The presence or absence of substituents at $R^3$, $R^4$, $R^5$, or $R^6$ does not appear to greatly affect activity(compare K3 and DH2 for example).

In one embodiment, each of $R^3$, $R^4$, $R^5$, and $R^6$ is independently —H, —OH, C$_{1-7}$alkyl, C$_{1-7}$alkoxy, or C$_{1-7}$alkylacyloxy.

In one embodiment, each of $R^3$, $R^4$, $R^5$, and $R^6$ is independently: —H; —OH; -Me, -Et, -nPr, -iPr, -nBu, -sBu, -iBu, -tBu; —OMe, —OEt, —O(nPr), —O(iPr), —O(nBu), —O(sBu), —O(iBu), —O(tBu); —OC(=O)Me, -OC(=O)Et, —OC(=O)(nPr), —OC(=O)(iPr), —OC(=O)(nBu), —OC(=O)(sBu), —OC(=O)(iBu), or —O(C=O)(tBu).

In one embodiment, each of $R^3$, $R^4$, $R^5$, and $R^6$ is independently: —H; —OH; -Me, -Et; —OMe, —OEt; —OC(=O)Me, or —OC(=O)Et.

In one embodiment, each of $R^3$, $R^4$, $R^5$, and $R^6$ is independently: —H; —OH; -Me; —OMe; or —OC(=O)Me.

In one embodiment, each of $R^3$, $R^4$, $R^5$, and $R^6$ is independently: —H or —OH.

In one embodiment, each of $R^4$, $R^5$, and $R^6$ is —H, and $R^3$ is as defined above:

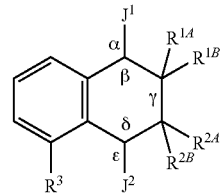

IX

In one embodiment, each of $R^4$, $R^5$, and $R^6$ is —H, and $R^3$ is —H:

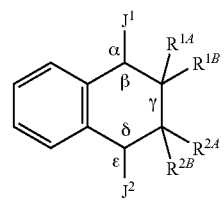

X

In this embodiment, each of $R^4$, $R^5$, and $R^6$ is —H, and $R^3$ is —OH.

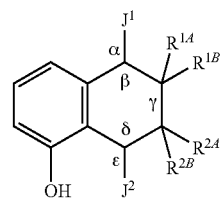

XI $J^1$ and $J^2$

As demonstrated in the examples, compounds in which $J^1$ and $J^2$ are both =O, or in which they are —$OR^7$ and —$OR^8$ respectively, may both have high activities (compare K3 and DH9 for example; also DH5).

Thus, referring to formula IV above, each of $R^7$ and $R^8$ is independently —H, $C_{1-7}$alkyl (including, e.g. unsubstituted $C_{1-7}$alkyl, substituted $C_{1-7}$alkyl such as $C_{1-7}$haloalkyl, $C_{1-7}$hydroxyalkyl, $C_{1-7}$aminoalkyl, $C_{1-7}$carboxyalkyl etc.), acyl (including, e.g., $C_{1-7}$alkylacyl, e.g., acetyl), —$SO_3H$, —$SO_3M$, or sulfonate.

The term "acyl," as used herein, pertains to a group —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)$CH_3$ (acetyl), —C(=O)$CH_2CH_3$ (propionyl), —C(=O)C($CH_3$)$_3$ (t-butyryl), and —C(=O)Ph (benzoyl, phenone).

In one embodiment, $R^7$ and $R^8$ are the same.

In one embodiment, $R^7$ and $R^8$ are different.

In one embodiment, each of $R^7$ and $R^8$ is independently —H, $C_{1-7}$alkyl, $C_{1-7}$alkylacyl, —$SO_3H$, —$SO_3M$, or $C_{1-7}$alkylsulfonate.

In one embodiment, each of $R^7$ and $R^8$ is independently —H; -Me, -Et, -nPr, -iPr, -nBu, -sBu, -iBu, -tBu; —C(=O)Me, —C(=O)Et, —C(=O)(nPr), —C(=O)(iPr), —C(=O)(nBu), —C(=O)(sBu), —C(=O)(iBu), or —(C=O)(tBu); —$SO_3H$, —$SO_3M$, —$SO_3$Me, —$SO_3$Et, —$SO_3$(nPr), —$SO_3$(iPr), —$SO_3$(nBu), —$SO_3$(sBu), —$SO_3$(iBu), or —$SO_3$(tBu).

In one embodiment, each of $R^7$ and $R^8$ is independently —H; -Me, -Et, —C(=O)Me, —C(=O)Et, —$SO_3H$, —$SO_3M$, —$SO_3$Me, or —$SO_3$Et.

In one embodiment, each of $R^7$ and $R^8$ is independently —H; -Me, —C(=O)Me, —$SO_3H$, —$SO_3M$, or —$SO_3$Me.

In one embodiment, each of $R^7$ and $R^8$ is —H:

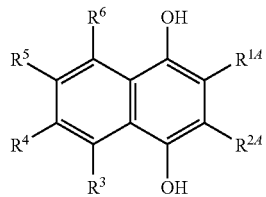

XII

Preferred compounds of the present invention are those which show high activity in the assays described herein, particularly 'cell based assay I' described below. Preferred compounds have a B50 of less than 10, more preferably less than 5. Likewise they will have a low toxicity, with an Rxindx of greater than 4, more preferably greater than 10.

As used hereinafter, unless context demands otherwise, the term "vitamin K compound" is intended to encompass any of these compounds such as (for example only) menadione, menadiol and diesters thereof, and analogs of any of these in accordance with the formulae given herein.

Uses of the Present Invention

In one aspect there is disclosed use of a vitamin K compound to inhibit the aggregation of a protein, which aggregation is associated with a disease state.

In general, the protein aggregation to which the present invention may be applied is that which arises from an induced conformational polymerisation interaction i.e. one in which a conformational change of the protein, or in a fragment thereof, gives rise to templated binding and aggregation of further (precursor) protein molecules in a self-propagating manner. Once nucleation is initiated, an aggregation cascade may ensue which involves the induced conformational polymerisation of further protein molecules, leading to the formation of toxic product fragments in aggregates which are substantially resistant to further proteolysis. The protein aggregates thus formed are thought to be a proximal cause of disease states manifested as neurodegeneration, clinical dementia, and other pathological symptoms.

Uses in Relation to Tau Protein

Preferred embodiments of the invention are based on inhibition of tau protein aggregation. Where used herein, the term "tau protein" refers generally to any protein of the tau protein family. Tau proteins are characterised as being one among a larger number of protein families which co-purify with microtubules during repeated cycles of assembly and disassembly (Shelanski et al. (1973) Proc. Natl. Acad. Sci. USA, 70., 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

MAP2 is the predominant microtubule-associated protein in the somatodendritic compartment (Matus, A., in "*Microtubules*" [Hyams and Lloyd, eds.] pp 155-166, John Wiley and Sons, N.Y.). MAP2 isoforms are almost identical to tau protein in the tandem repeat region, but differ substantially both in the sequence and extent of the N-terminal domain (Kindler and Garner (1994) Mol. Brain Res. 26, 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation and so on.

Other Proteins

FIG. 4 shows a Table listing various other disease-associated aggregating proteins, the inhibition of which forms part of the present invention. In each case the disease or diseases in which the initiation of aggregation and\or mutation of the protein(s) may play a role is also listed.

As can be seen from the table, example diseases which are characterised by pathological protein aggregation include motor neurone disease and Lewy body disease. Furthermore, the pathogenesis of neurodegenerative disorders such as Pick's disease and Progressive Supranuclear Palsy appears to correlate with an accumulation of pathological tau aggregates in the dentate gyrus and stellate pyramidal cells of the neocortex, respectively (Wischik et al. 2000, loc. cit). Other 'tauopathies' to which the present invention may be applied include Familial Multiple System Tauopathy, Corticobasal Degeneration, and Familial Gerstmann-Straussler-Scheinker Disease.

Thus it will be appreciated, in the light of the above discussion, (and except where context requires otherwise) where the embodiments of the invention are described with respect to tau protein or tau-like proteins (e.g. MAP2) the description should be taken as applying equally to the other proteins discussed above (e.g. β-amyloid, synuclein, prion etc.) or other proteins which may initiate or undergo a similar pathological aggregation by virtue of conformational change in a domain critical for propagation of the aggregation, or which imparts proteolytic stability to the aggregate thus formed (article by Wischik et al. (in "Neurobiology of Alzheimer's Disease", 2nd Edition (2000) Eds. Dawbarn, D. and Allen, S. J., The Molecular and Cellular Neurobiology Series, Bios Scientific Publishers, Oxford). All such proteins may be referred to herein as "aggregating disease proteins." The diseases may be referred to herein as "diseases of protein aggregation".

Likewise, where mention is made herein of "tau-tau aggregation", or the like, this may also be taken to be applicable to other aggregation of other proteins which have similar properties in this respect, such as β-amyloid aggregation, prion aggregation and synuclein aggregation etc. Likewise "tau proteolytic degradation" and so on.

Other Uses and Methods

As described above, in one aspect there is disclosed use of a vitamin K compound to inhibit the aggregation of a protein, which aggregation is associated with a disease state as described above.

A further embodiment is a method of treatment or prophylaxis of a disease of protein aggregation as described above, which method comprises administering to a subject a vitamin K compound, or therapeutic composition comprising the same, such as to inhibit the aggregation of the protein associated with said disease state.

In a further embodiment there is disclosed a Vitamin K compound, or therapeutic composition comprising the same, for use in a method of treatment or prophylaxis of a disease of protein aggregation as described above, which method comprises administering to a subject the vitamin K compound or composition such as to inhibit the aggregation of the protein associated with said disease state.

In a further embodiment there is disclosed use of a Vitamin K compound in the preparation of a medicament for use in a method of treatment or prophylaxis of a disease of protein aggregation as described above, which method comprises administering to a subject the medicament such as to inhibit the aggregation of the protein associated with said disease state.

In one embodiment there is disclosed a method of regulating the aggregation of a protein in the brain of a mammal, which aggregation is associated with a disease state as described above, the treatment comprising the step of administering to said mammal in need of said treatment, a prophylactically or therapeutically effective amount of an inhibitor of said aggregation, wherein the inhibitor is a Vitamin K compound.

In another embodiment of the present invention, there is provided a method of inhibiting production of protein aggregates (e.g. in the form of PHFs, optionally in NFTs) in the brain of a mammal, the treatment being as described above.

Vitamin K compounds may be administered alone, or in combination with other treatments, either simultaneously or sequentially, dependent upon the condition or disease to be treated. In particular it may be desired to use or formulate Vitamin K compounds with other inhibitors of the relevant protein aggregation reaction e.g. in the case of Tau this may be compounds as described in WO 96/30766 or prior filed, unpublished application GB 0101049.5, the contents of which are incorporated herein by reference.

Other therapeutic agents for treating e.g. AD with which the present invention may be combined include cholinesterase inhibitors such as donepezil, muscarinic receptor agonists, and inhibitors of beta-amyloid.

A further aspect of the present provides a therapeutic combination composition comprising a vitamin K compound plus one further compound.

Dosage of Therapeutics

Administration of compounds, compositions or medicaments as described herein is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of the disease being treated.

Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

Typically the mammal will be human, although use in animals (e.g. for test purposes, or veterinary therapeutic purposes) is also embraced by the invention.

The recommended daily allowances for Vitamin K vary between about 10-20 μg/day (infant); 15-60 μg/day (children and youths up to 11 years), and 50-140 μg/day (children over 11 years and adult) (RDAs for US, 1980). Other reports recommend 0.01-0.03 mg/kg body weight (see Friedrich, 1988, loc cit, discussion page 319-320). Vitamin K-type compounds, such as those used in the present invention, may be administered in an amount greater than or equal to about 10 mg/per day or more for a 70 kg adult (according to British National Formulary data released by the BMA and Royal Pharmaceutical Society of Great Britain).

Formulation and Administration of Therapeutics

Suitable compounds, such as those with a formula as shown above or their pharmaceutically-acceptable salts, may be incorporated into compositions of this aspect of the present invention after further testing for toxicity.

The compositions may include, in addition to the above constituents, pharmaceutically-acceptable excipients, preserving agents, solubilizers, viscosity-increasing substances, stabilising agents, wetting agents, emulsifying agents, sweetening agents, colouring agents, flavouring agents, salts for varying the osmotic pressure, buffers, or coating agents. Such materials should be non-toxic and should not interfere with the efficacy of the active ingredient. The precise nature of the carrier or other material may depend on the route of administration. Examples of techniques and protocols can be found in "Remington's Pharmaceutical Sciences", 16$^{th}$ edition, Osol, A. (ed.), 1980. Compounds affecting the stability of menadione (vitamin k3) are discussed by Daabis & Khawas (1969 Pharmazie 24, 750) and Fattah and Daabis (1977 Pharmazie 32 H.4, 232).

Where the composition is formulated into a pharmaceutical composition, the administration thereof can be effected parentally such as orally, in the form of powders, tablets, coated tablets, dragees, hard and soft gelatine capsules, solutions, emulsions or suspensions, nasally (e.g. in the form of nasal sprays) or rectally (e.g. in the form of suppositories). However, the administration can also be effected parentally such as intramuscularly, intravenously, cutaneously, subcutaneously, or intraperitoneally (e.g. in the form of injection solutions).

Thus, for example, where the pharmaceutical composition is in the form of a tablet, it may include a solid carrier such as gelatine or an adjuvant. For the manufacture of tablets, coated tablets, dragees and hard gelatine capsules, the active compounds and their pharmaceutically-acceptable acid addition salts can be processed with pharmaceutically inert, inorganic or organic excipients. Lactose, maize, starch or derivatives thereof, talc, stearic acid or its salts etc. can be used, for example, as such excipients for tablets, dragees and hard gelatine capsules. Suitable excipients for soft gelatine capsules are, for example, vegetable oils, waxes, fats, semi-solid and liquid polyols etc. Where the composition is in the form of a liquid pharmaceutical formulation, it will generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may also be included. Other suitable excipients for the manufacture of solutions and syrups are, for example, water, polyols, saccharose, invert sugar, glucose, trihalose, etc. Suitable excipients for injection solutions are, for example, water, alcohols, polyols, glycerol, vegetable oils, etc. For intravenous, cutaneous or subcutaneous injection, or intracatheter infusion into the brain, the active ingredient will be in the form of a parenterally-acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers and/or other additives may be included, as required.

Oral and parental preparations of vitamin K1 and of vitamin K3 are available commercially (albeit not for the uses disclosed herein).

The disclosure of any cross-reference made herein, inasmuch as it may be required by one skilled in the art to supplement the present disclosure, is hereby specifically incorporated herein.

The invention will now be further described with reference to the following non-limiting Figures and Examples. Other embodiments of the invention will occur to those skilled in the art in the light of these.

FIGURES

FIG. 1—shows in vitro tau-tubulin binding in the presence of Vitamin K2.

FIG. 2a shows the structures of vitamins K1-K3 and 2,3-dimethyl-1,4-naphthoquinone (denoted DH10).

FIG. 2b shows two 5-hydroxy 1,4-naphthoquinone derivatives (denoted DH14 and DH2). A further compound (denoted DH16) is included for comparison.

FIG. 2c shows the effect of the presence of a hydroxy in the 2' position in three compounds (denoted DH15, DH7, and DH1).

FIG. 2d shows the effect of the presence of a sulphate and bisulphite group in the 2' position (compounds denoted DH8, DH3). Also shown is an alkoxy derivative of the present invention (DH17), and a further compound (denoted DH19, which includes a halide) which is included for comparison.

FIG. 2e shows two 1,4-naphthoquinols were examined (compounds denoted DH4, DH5).

FIG. 2f shows the effect of acetate and sulphate substitutions (compounds denoted DH9, DH11, DH13).

FIG. 2g shows the effect of alkoxy and methyl substitutions (compound denoted DH18) and a further compound (denoted DH20, which includes a halide) which is included for comparison.

FIG. 4 shows a Table listing various other disease-associated aggregating proteins which may be used in the present invention.

Figure 5:
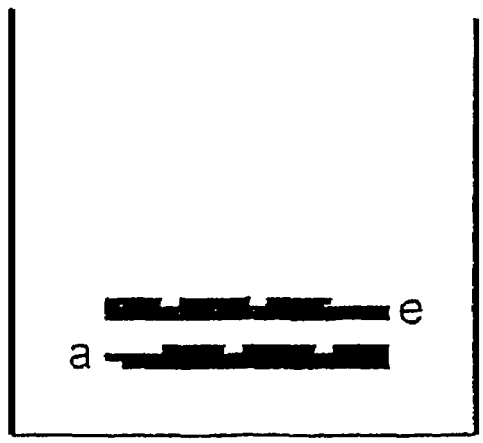

FIG. 5 is a schematic representation of the in vitro aggregation assay of WO 96/30766 in which binding of two truncated units is measured. The species terminating at Ala-390 ("a") is first coated on the ELISA plate (in sodium carbonate buffer: 50 mM, pH 9.6). Next, a second truncated tau species terminating at Glu-391 ("e") is incubated in various buffer conditions. Only the species "e" is recognised by mAb 423, and hence mAb 423 immunoreactivity measures only that tau which is bound during the second incubation.

Figure 6A:
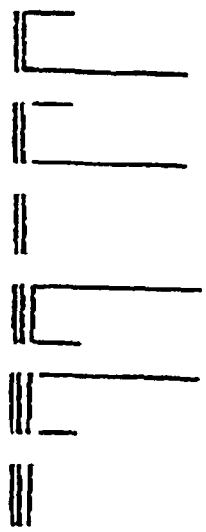

FIG. 6a is a schematic representation of the process upon which cell-based assay I ('T40/12 kD') is based. It shows how induction of full-length tau can lead to its conversion into the 12 kD fragment, provided there is some preexisting 12 kD tau in the cell. FIGS. 6b-e are examples results obtained from the assay using DH15 (negative result), vitamin K3, DH9 and DH17.

Figure 7A:
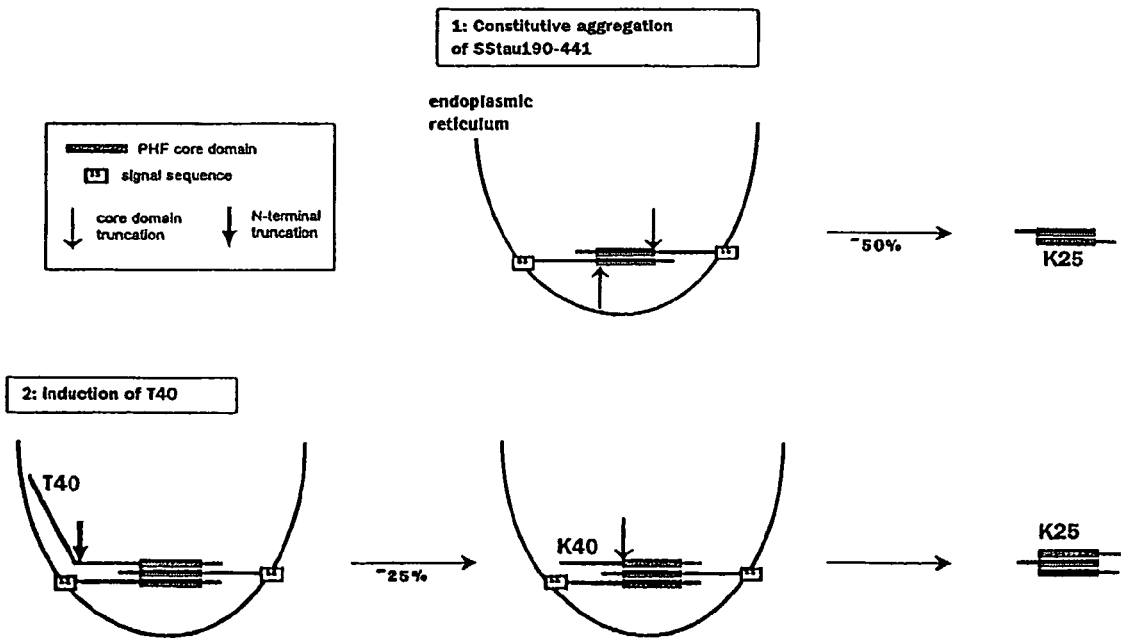
Figure 7B:
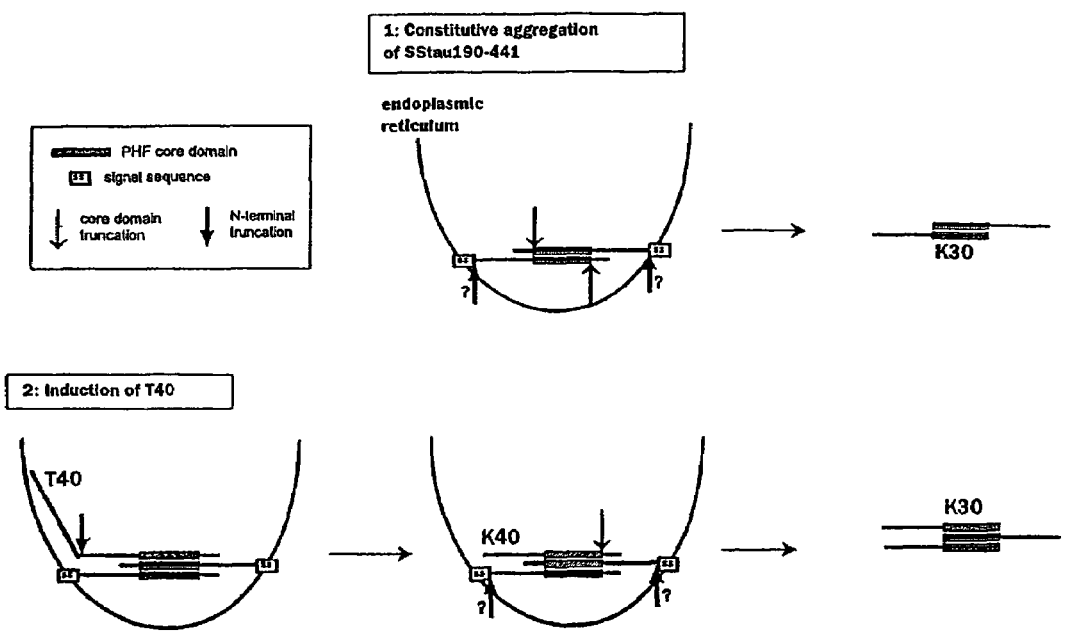

FIG. 7 is a schematic representation of the cell-based assay II ('SSK40/25 kD').

EXAMPLES

Methods

In Vitro Assay

This is described in detail in WO 96/30766. Briefly, a fragment of tau corresponding to the core repeat domain, which has been adsorbed to a solid phase substrate, is able to capture soluble full-length tau and bind tau with high affinity. This association confers stability against proteolytic digestion of the aggregated tau molecules. The process is self-propagating, and can be blocked selectively by prototype pharmaceutical agents (Wischik, C. M., et al. (1996), loc. cit).

The assay is shown schematically in FIG. 5.

Cell-based Assay I ('T40/12 kD')

In essence, fibroblast cells (3T6) express full-length tau ("T40") under control of an inducible promotor, and low constitutive levels of the PHF-core tau fragment (12 kD fragment). When T40 expression is induced, it undergoes aggregation-dependent truncation within the cell, N-terminally at ~αα 295 and C-terminally at ~αα 390, thereby producing higher levels of the 12 kD PHF-core domain fragment. Production of the 12 kD fragment can be blocked in a dose-dependent manner by tau-aggregation inhibitors. Indeed the quantitation of inhibitory activity of compounds with respect to proteolytic generation of the 12 kD fragment within cells can be described entirely in terms of the same parameters which describe inhibition of tau-tau binding in vitro. That is, extent of proteolytic generation of the 12 kD fragment within cells is determined entirely by the extent to tau-tau binding through the repeat domain. The availability of the relevant proteases within the cell is non-limiting.

Figure 6B:
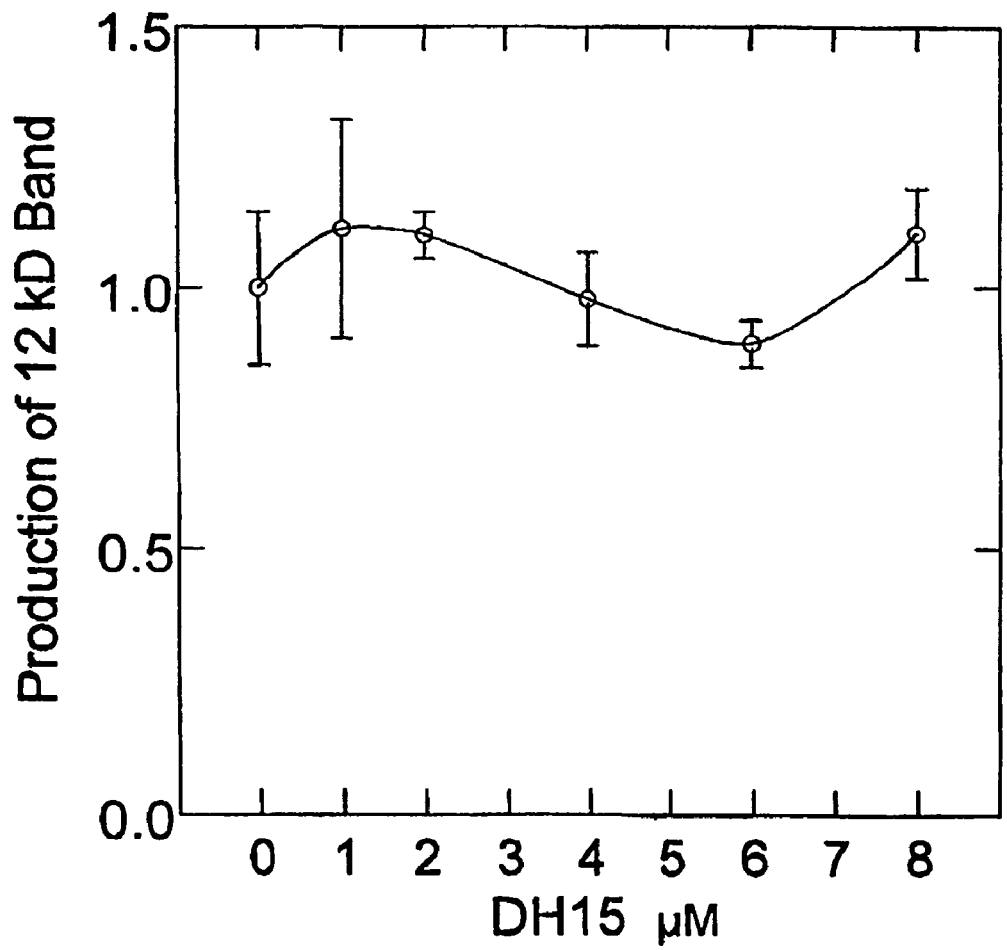
Figure 6C:
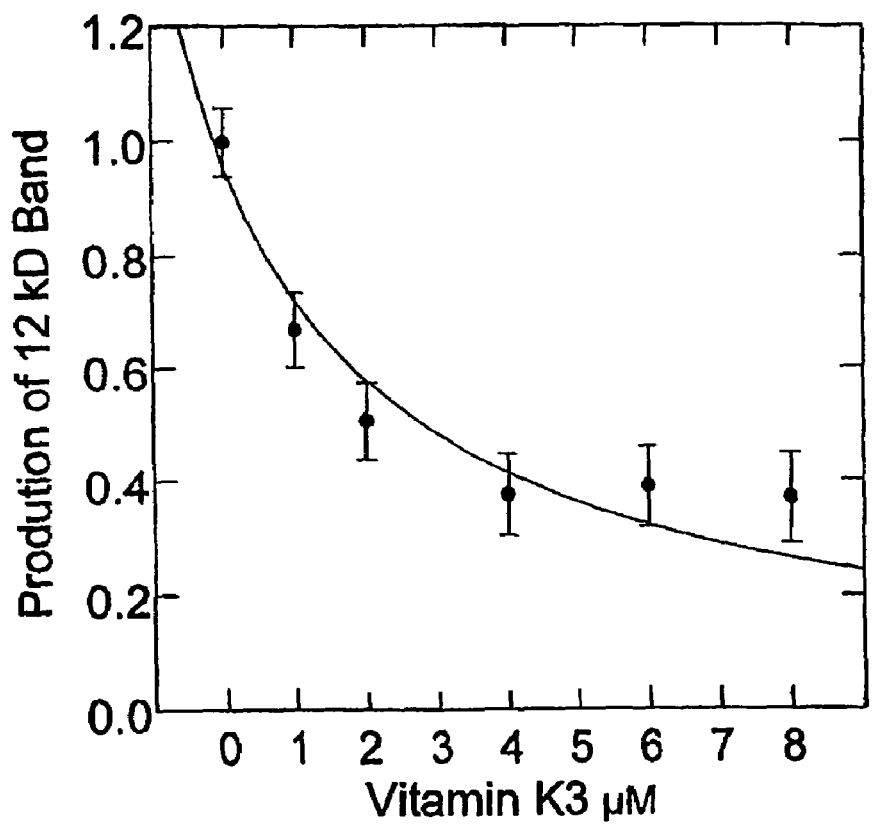
Figure 6D:
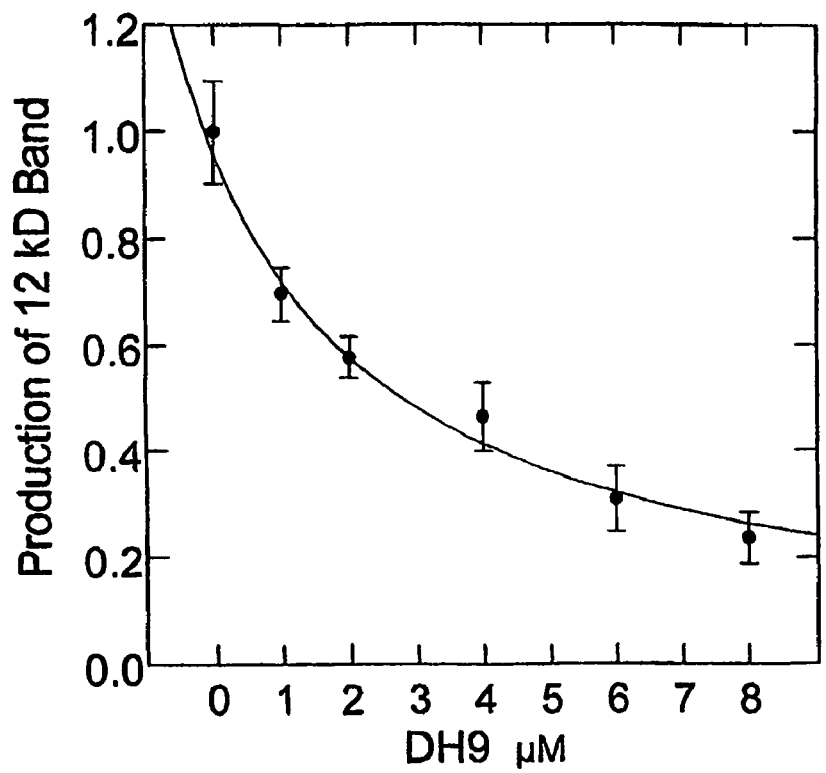
Figure 6E:
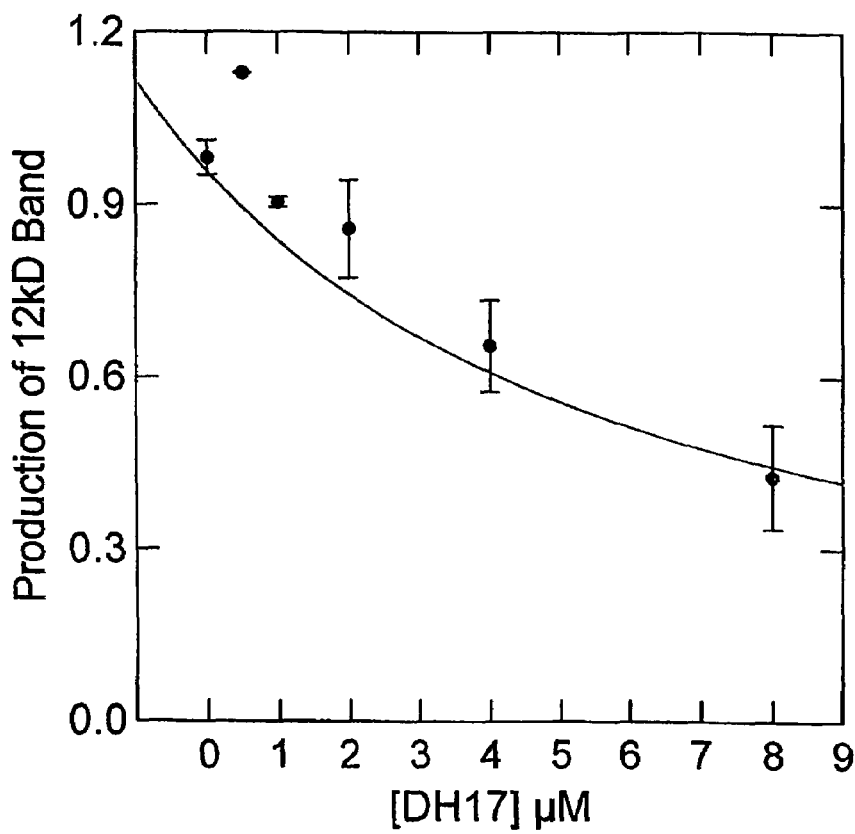

The process is shown schematically in FIG. 6a, with example results being shown in FIGS. 6b-6d. The process is described in more detail in prior filed unpublished application GB 0101049.5.

Parameters Used in Cell-based Assay I

The observed cell data for production of the 12 kD band can be fitted closely (i.e. observed vs. predicted correlation coefficient >0.9), to a standard function describing inhibition of tau-tau binding in vitro. To obtain this fit, two assumptions need to be made, which are consistent with results from other cell-based and in vitro studies:

1) the intracellular concentration of tau is approximately 500 nM;
2) the tau-tau binding affinity is 22 nM.

When these assumptions are made, the function:

Activity=[tau]([tau]+$Kd$*(1+[inhibitor]/$KI$))

can be solved by standard numerical methods to derive a value for apparent KI. Comparison with values observed for tau-tau binding in vitro at a tau concentration of 500 nM, where the Kd value for tau-tau binding is known to be 22 nM confirm that the sole determinant of production of the proteolytically stable core tau unit of the PHF within the cell is simply the extent of tau-tau binding.

A further parameter, B50, has been established in respect of compounds exemplified herein. The B50 value is the determined concentration of test compound used in the cell assay at which relative production of the 12 kD band from full-length tau was reduced to 50% of that observed in the absence of the compound. This provides an indication of the tissue concentration which would be required to achieve the corresponding activity in vivo. In general there is an approximately linear relationship between apparent KI value and B50 value, which can be used to derive the KI value:

$B50$(μM)=0.0217×$KI$(nM)

Cell-based Assay II('ssK40/25 kD')

The process is described in more detail in prior filed unpublished application GB 0100119.7. As demonstrated therein, the constitutive expression of membrane-targeted tau (ss-tau190-441, "ssK40") results in production of two specific cleavage products: a minor 30 kD species ("K30") in which the fragment is C-terminally truncated at residue ~390, and a major 25 kD species ("K25") in which the fragment is N-terminally truncated at residue ~295. These cleavage sites correspond to the known boundaries of the PHF-core domain, indicate that their generation within the cell depends on PHF-like tau aggregation through an antiparallel phase-shifted alignment of the repeat domain.

This is shown schematically in FIG. 7. When expression of full-length tau (T40) is activated under control of an inducible promoter in cells which constitutively express the membrane-targeted ssK40 fragment, T40 is processed proteolytically to give rise to a K40 fragment (N-terminal truncation at ~αα 185), a K30 fragment (C-terminal truncation ~αα 390) and a K25 fragment (N-terminal truncation at ~αα 295).

Example 1

In Vitro Tau-tau and Tau-tubulin Binding

Figure 1:
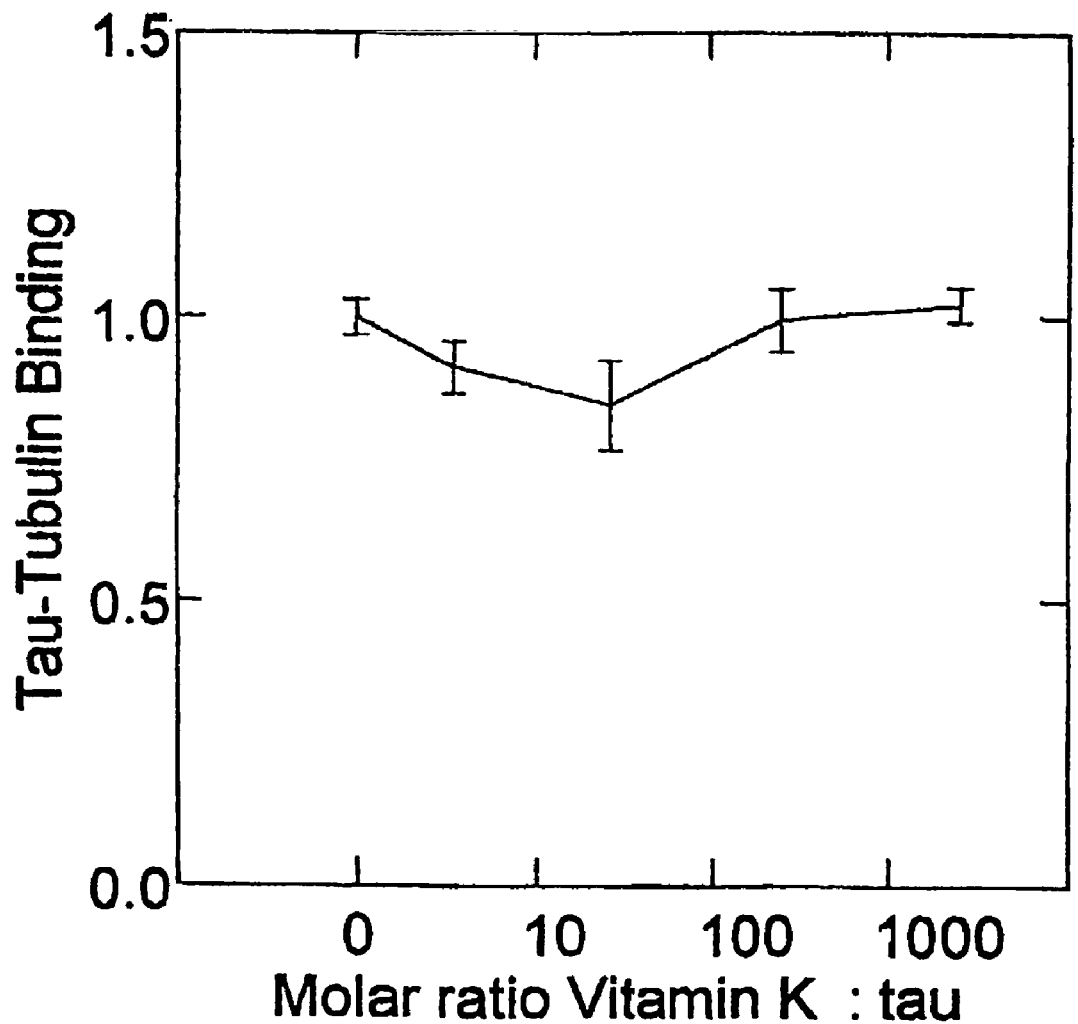

Vitamin K2 was found to have some activity in the tau-tau binding assay in vitro. For values less than 100 μM, the apparent KI value in vitro is 942 nM. However, Vitamin K2 does not inhibit tau-tubulin binding in vitro at concentrations up to 500 μM (i.e. 2500:1 molar ratio with respect to tau in the conditions of the assay)—see FIG. 1.

Further data (not shown) demonstrated that DH3 (FIG. 2d) caused inhibition at concentrations greater than or equal to 50 μM (with tau concentration 100 nm). However menadione (FIG. 2a) did not show activity in the in vitro assay, possibly due to its reduced solubility.

On this basis, further structure-activity characterisation was undertaken using the cell based assays which can be more readily used with compounds of different solubilities.

Example 2

Tau-tau Inhibition Using Cell Based Assay I

FIG. 2a shows the structures of vitamins K1-K3 and 2,3-dimethyl-1,4-naphthoquinone (denoted DH10) which is closely related to K3 (2-methyl-1,4-naphthoquinone(menadiol)).

The corresponding values are listed for apparent KI and B50 calculated from the cell data using the T40/12 kD cell assay to determine extent of inhibition of tau-tau binding as described above.

By comparing structures with inhibitory activity in cells, it is apparent that longer side-chains at the 3' position are associated with reduced activity.

FIG. 2b shows two 5-hydroxy 1,4-naphthoquinone derivatives. Comparison of DH14 and DH2 suggests that the methyl group in the 3' position may be preferred to enhance activity, and that the hydroxy group in the 5' position is not detrimental. DH2 proved to be the most highly toxic of all the compounds tested, with a cellular LD50 value of 2.1 μM. The DH16 compound did not show any activity.

FIG. 2c shows the effect of the presence of a hydroxy in the 2' position in three compounds. As can be seen from DH15 and DH17, a hydroxy in the 2' position appears to be detrimental to activity. However, weak activity can be observed with the 3-prenyl derivative (DH1).

FIG. 2d shows the effect of the presence of a sulphate group in the 2' position. As can be seen, a sulphate group can be accommodated in this position without substantial loss of activity. However the bisuphite (a form of K3 widely used as an animal food supplement) has reduced activity. The methoxy derivative (DH17) showed good activity, as expected by comparison with vitamin $K_3$ in FIG. 2a. The compound shown as DH19 showed no activity as an inhibitor of aggregation, and indeed it appeared that it may be a pro-aggregant (results not shown). This suggests that compounds having the enolisation properties of DH19 may be undesirable.

FIG. 2e shows the results obtained when two 1,4-naphthoquinols were examined. The dicarbonitrile was entirely inactive, the naphthoic acid form had activity in preliminary experiments. Naphthoic acid is generally present in vegetables, and is the natural precursor for synthesis of the higher naphthoquinones in leafy vegetables and bacteria.

FIG. 2f shows the effect of acetate and sulphate substitutions in the 1 and 4 positions. As can be seen from this series, the 2-methyl diacetate (DH9) is highly active, whereas the 2,3-dimethyl diacetate (DH11) has reduced activity, as with the corresponding naphthoquinones. The 2-methyl disulphate is intermediate in activity.

FIG. 2g shows a compound related to DH10 in FIG. 2a, but wherein a methyl group has been replaced with a methoxy (DH18). Again this has activity (cf. DH17 and K3). The compound shown as DH20 showed no activity as an inhibitor of aggregation, and indeed it appeared that it may be a pro-aggregant (results not shown).

Example 3

Tau-tau Inhibition Using Cell Based Assay II

To confirm the results obtained using cell based assay I, further experiments were performed with cell based assay II.

Figure 3A:
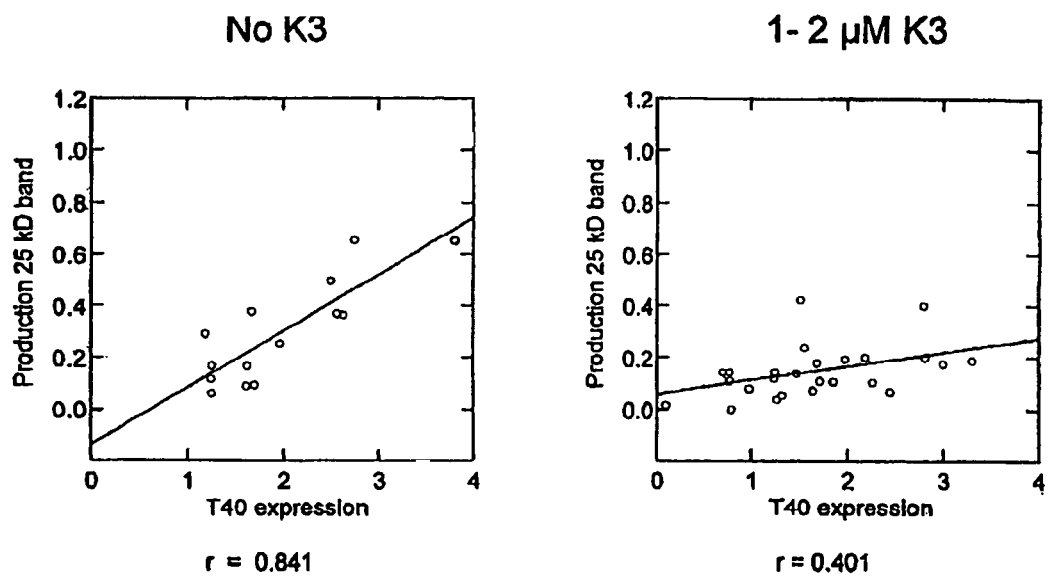
FIGS. 3a and 3b show the tau-tau aggregation inhibition using cell based assay II.
Figure 3B:
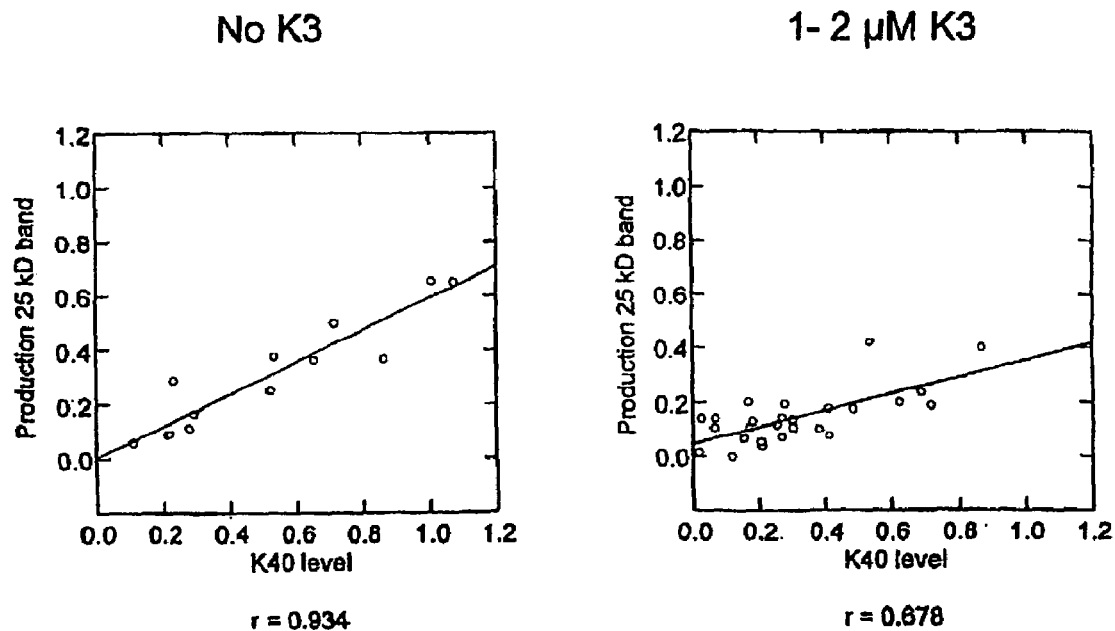

FIGS. 3a and 3b show that this proteolytic processing can be blocked in this system using Vitamin K3 (menadione) at concentrations of 1-2 µM. FIG. 3a shows that the conversion of T40→K25 is reduced to about ¼ of that seen without K3, and FIG. 3b shows that the conversion K40→K25 is reduced to about ½ of that seen without K3. From this it can be inferred that the conversion of T40→K40 is also reduced to about ½ of that seen without K3.

Example 4

Toxicity Using Cell Based Assay I

Toxicity of the compounds described above was assessed in the T40/12 kD cell assay used to assess activity. Toxicity was measured by cell numbers after 24 hrs exposure to the compound using a lactate dehydrogenase assay kit TOX-7 (Sigma Biosciences) according to the manufacturer's instructions after lysis of remaining cells. Alternatively a kit from Promega UK (CytoTox 96) was used, again according to the manufacturer's instructions.

Two important conclusions emerge from this analysis:
1. There is no correlation between activity of compounds as inhibitors of tau-tau aggregation and their toxicity in the assay;
2. Considering the compounds tested so far, several have similar KI values of about 120 nM corresponding to a B50 cellular activity level of 2.6 µM. However they do differ in relative toxicity, as expressed by the LD50 value. A preferred compound in this group for clinical use may be that which has the highest LD50 value. A therapeutic index (RxIndx) has been calculated for each of compounds tested in the cell assays as follows:

$$RxIndx = LD50/B50$$

Certain compounds described above can be arranged in order:

| Compound | KI (nM) | B50 (µM) | r* | LD50 (µM) | Rxindx |
|---|---|---|---|---|---|
| K3 | 128 | 2.78 | 0.925 | 44.92 | 16.17 |
| DH10 | 221 | 4.80 | 0.935 | 66.71 | 13.91 |
| DH5 | 118 | 2.56 | 0.776 | 34.29 | 13.39 |
| DH1 | 513 | 11.13 | 0.864 | 100.97 | 9.07 |
| DH8 | 157 | 3.41 | 0.964 | 18.55 | 5.45 |
| DH13 | 263 | 5.71 | 0.956 | 30.90 | 5.41 |
| DH9 | 127 | 2.76 | 0.988 | 13.09 | 4.75 |
| DH3 | 630 | 13.68 | 0.944 | 63.36 | 4.63 |
| DH11 | 674 | 14.63 | 0.950 | 12.13 | 0.83 |

*is an indication of the goodness of fit of the function to the data.

References for FIG. 4:

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F. & Pepys, M. B. (1997) Instability, unfolding and aggregation of human lysozyme variants underlying amyloid fibrillogenesis. *Nature* 385, 787-793.

Carrell, R. W. & Gooptu, B. (1998) Conformational changes and disease—serpins, prions and Alzheimer's. *Current Opinion in Structural Biology* 8, 799-809.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences, USA* 96, 3590-3594.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. *Nature* 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. *Science* 277, 1990-1993.

Dische, F. E., Wernstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. *Diabetologia* 31, 158-161.

Gasset, M., Bladwin, M. A., Lloyd, D. H., abriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullan, M., Brown, J., Crawford, F., Fidani, L., Giuffra, L., Haynes, A., Irving, N., James, L., Mant, R., Newton, P., Rooke, K., Roques, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. *Nature* 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429. Gustavsson, A., Engström, U. & Westermark, P. (1991) Normal transthyretin and synthetic transthyretin fragments form amyloid-like fibrils in vitro. *Biochemical and Biophysical Research Communications* 175, 1159-1164.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Johansson, B., Wernstedt, C. & Westermark, P. (1987) Atrial natriuretic peptide deposited as atrial amyloid fibrils. *Biochemical and Biophysical Research Communications* 148, 1087-1092.

Lomas, D. A., Evans, D. L., Finch, J. T. & Carrell, R. W. (1992) The mechanism of Z al-antitrypsin accumulation in the liver. *Nature* 357, 605-607.

Maury, C. P. & Baumann, M. (1990) Isolation and characterization of cardiac amyloid in familial amyloid polyneuropathy type IV (Finnish): relation of the amyloid protein to variant gelsolin. *Biochimica et Biophysica Acta* 1096, 84-86.

Paulson, H. L. (1999) Human genetics '99: trinucleotide repeats. *American Journal of Human Genetics* 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. *Nature* 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di Iorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Sletten, K., Westermark, P. & Natvig, J. B. (1976) Characterization of amyloid fibril proteins from medullary carcinoma of the thyroid. *Journal of Experimental Medicine* 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. *Proceedings of the National Academy of Sciences, USA* 95, 6469-6473.

Uemichi, T., Liuepnicks, J. j. & Benson, M. D. (1994) Hereditary renal amyloidosis with a novel variant fibrinogen. *Journal of Clinical Investigation* 93, 731-736.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H., O'Brien, T. D. & Betsholtz, C. (1992) Islet amyloid polypeptide—a novel controversy in diabetes research. *Diabetologia* 35, 297-303.

Westermark, P., Johnson, K. H. & Pitkanen, P. (1985) Systemic amyloidosis: A review with emphasis on pathogenesis. *Applied Physiology* 3, 55-68.

Wischik, C. M., Novak, M., Thøgersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

The invention claimed is:

1. A method of treatment of a neurodegenerative disease or clinical dementia, either being associated with tau protein aggregation, which method comprises administering to a subject a therapeutically effective amount of a compound, wherein the compound is selected from a compound of formula II:

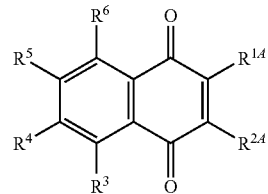

wherein $R^{1A}$ is —OMe, —OC(=O)Me, —COOH, —COOMe, —SO$_3$H, —SO$_3$M, or —SO$_3$Me;

$R^{2A}$ is —H, unsubstituted $C_{1-7}$ alkyl, $C_{1-7}$ haloalkyl, $C_{1-7}$ hydroxyalkyl, $C_{1-7}$ aminoalkyl, $C_{1-7}$ carboxyalkyl, —OH, $C_{1-7}$ alkoxy, acyloxy, —COOH, ester, —SO$_3$H, —SO$_3$M, sulfonate, $C_{1-7}$ alkylsulfonate, or a short chain alkyl group;

$R^3$, $R^4$, $R^5$, and $R^6$ are independently —H, —OH, $C_{1-7}$ alkyl, $C_{1-7}$ alkoxy or acyloxy; and, M denotes a cation or cations of charge or cumulative charge to counter the charge on the —SO$_3$— group;

or a compound of formula III:

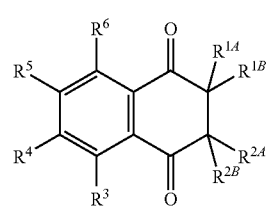

or a compound of formula IV:

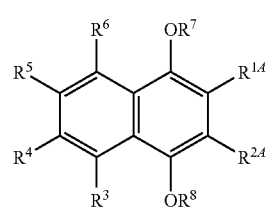

wherein for formula III or IV:
either
(A) $R^{1A}$ is unsubstituted $C_{1-7}$ alkyl, $C_{1-7}$ haloalkyl, $C_{1-7}$ hydroxyalkyl, $C_{1-7}$ aminoalkyl, $C_{1-7}$ carboxyalkyl, —OH, $C_{1-7}$ alkoxy, acyloxy, —COOH, ester, —SO$_3$H, —SO$_3$M, sulfonate, $C_{1-7}$ alkylsulfonate, or a short chain alkyl group; and $R^{2A}$ is —H, unsubstituted $C_{1-7}$ alkyl, $C_{1-7}$ haloalkyl, $C_{1-7}$ hydroxyalkyl, $C_{1-7}$ aminoalkyl, $C_{1-7}$ carboxyalkyl, —OH, $C_{1-7}$ alkoxy, acyloxy, —COOH, ester, —SO$_3$H, —SO$_3$M, sulfonate, $C_{1-7}$ alkylsulfonate, or a short chain alkyl group;

or (B) $R^{1A}$ is —H, unsubstituted $C_{1-7}$ alkyl, $C_{1-7}$ haloalkyl, $C_{1-7}$ hydroxyalkyl, $C_{1-7}$ aminoalkyl, $C_{1-7}$ carboxyalkyl, —OH, $C_{1-7}$ alkoxy, acyloxy, —COOH, ester, —SO$_3$H, —SO$_3$M, sulfonate, $C_{1-7}$ alkylsulfonate, or a short chain alkyl group; and $R^{2A}$ is unsubstituted $C_{1-7}$ alkyl, $C_{1-7}$ haloalkyl, $C_{1-7}$ hydroxyalkyl, $C_{1-7}$ aminoalkyl, $C_{1-7}$ carboxyalkyl, —OH, $C_{1-7}$ alkoxy, acyloxy, —COOH, ester, —SO$_3$H, —SO$_3$M, sulfonate, $C_{1-7}$ alkylsulfonate, or a short chain alkyl group;

$R^{1B}$, if present, is —H, unsubstituted $C_{1-7}$alkyl, $C_{1-7}$haloalkyl, $C_{1-7}$hydroxyalkyl, $C_{1-7}$aminoalkyl, $C_{1-7}$carboxyalkyl, —OH, $C_{1-7}$alkoxy, acyloxy, —COOH, ester, —SO$_3$H, —SO$_3$M, sulfonate, $C_{1-7}$alkylsulfonate, or a short chain alkyl group;

$R^{2B}$, if present, is —H, unsubstituted $C_{1-7}$alkyl, $C_{1-7}$haloalkyl, $C_{1-7}$hydroxyalkyl, $C_{1-7}$aminoalkyl, $C_{1-7}$carboxyalkyl, —OH, $C_{1-7}$alkoxy, acyloxy, —COOH, ester, —SO$_3$H, —SO$_3$M, sulfonate, $C_{1-7}$alkylsulfonate, or a short chain alkyl group;

$R^3$, $R^4$, $R^5$, and $R^6$ is independently —H, —OH, $C_{1-7}$alkyl, $C_{1-7}$alkoxy, or acyloxy; and, $R^7$ and $R^8$ is independently —H, $C_{1-7}$alkyl, acyl, —SO$_3$H, —SO$_3$M, or sulfonate;

M denotes a cation or cations of charge or cumulative charge to counter the charge on the —SO$_3$ group;

and a pharmaceutically acceptable salt thereof, or a therapeutic composition comprising the same, such as to inhibit the aggregation of the protein associated with said disease or dementia.

2. A method as claimed in claim 1 wherein the compound is used in combination with another treatment for said disease or dementia.

3. A method as claimed in claim 1 wherein the disease is selected from the list consisting of Familial Multiple System Tauopathy, Corticobasal Degeneration, Familial Gerstmann-Straussler-Scheinker Disease, Motor Neurone Disease; Lewy body disease; Pick's disease; Progressive Supranuclear Palsy; Alzheimer's disease.

4. The method as claimed in claim 1 wherein the compound is one according to formula IV.

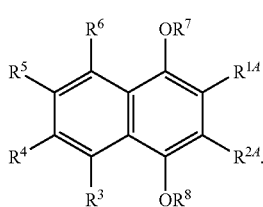

IV

5. The method as claimed in claim 4 wherein each of $R^7$ and $R^8$ is independently —H, -Me, -Et, —C(═O)Me, —C(═O)Et, —SO$_3$H, —SO$_3$M, —SO$_3$Me, or —SO$_3$Et.

6. The method as claimed in claim 5 wherein each of $R^7$ and $R^8$ is independently —H, -Me, —C(═O)Me, —SO$_3$H, —SO$_3$M, or —SO$_3$Me.

7. The method as claimed in claim 5 wherein each of $R^7$ and $R^8$ is —H.

8. The method as claimed in claim 1 wherein the compound has the formula II:

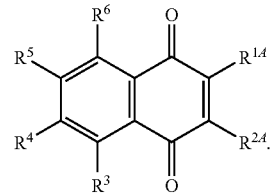

II

9. The method as claimed in claim 1 wherein the compound has the formula III:

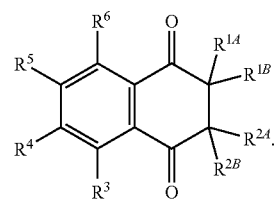

III

10. A method as claimed in claim 9 wherein $R^{1B}$ and $R^{2B}$ are both —H:

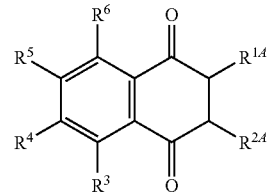

VIII

11. The method as claimed in claim 9 wherein $R^{2A}$ and $R^{2B}$ are both —H:

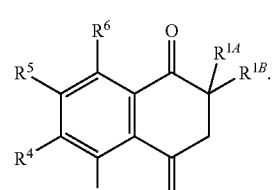

VII

12. The method as claimed in claim 1 wherein the short chain alkyl group in $R^{2A}$ is one of the following groups, where n is 0, 1, or 2:

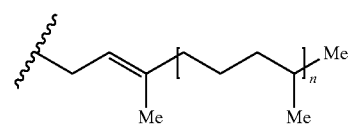

-continued

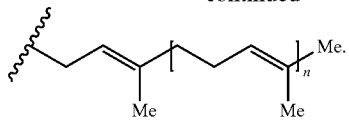

13. The method as claimed in claim 1 wherein for each of $R^{1A}$, $R^{2A}$, and $R^{1B}$ and $R^{2B}$ if present:
unsubstituted $C_{1-7}$-alkyl is selected from -Me, -Et, -nPr, -iPr, -nBu, -sBu, -iBu; and -tBu;
$C_{1-7}$-alkoxy is selected from —OMe, —OEt, —O(nPr), —O(iPr), —O(nBu), —O(sBu), —O(iBu), and —O(tBu);
acyloxy is selected from —OC(=O)Me, —OC(=O)Et, —OC(=O)(nPr), —OC(=O)(iPr), —OC(=O)(nBu), —OC(=O)(sBu), —OC(=O)(iBu), and —O(C=O)(tBu);
ester is selected from —C(=O)OMe, —C(=O)OEt, —C(=O)O(nPr), —C(=O)O(iPr), —C(=O)O(nBu), —C(=O)O(sBu), —C(=O)O(iBu), and —C(=O)O(tBu);
$C_{1-7}$alkylsulfonate is selected from —SO$_3$Me, —SO$_3$Et, —SO$_3$(nPr), —SO$_3$(iPr), —SO$_3$(nBu), —SO$_3$(sBu), —SO$_3$(iBu), and —SO$_3$(tBu),
short chain alkyl group is $CH_2CH=C(CH_3)_2$, and
wherein if the compound is a compound of formula II, then:
$R^{1A}$ is: —OMe, —OC(=O)Me, —COOMe, —SO$_3$H, —SO$_3$M, or —SO$_3$Me.

14. The method as claimed in claim 13
wherein for each of $R^{1A}$, $R^{2A}$, and $R^{1B}$ and $R^{2B}$ if present,
unsubstituted $C_{1-7}$-alkyl is selected from -Me and -Et,
$C_{1-7}$-alkoxy is selected from —OMe and —OEt, acyloxy is selected from —OC(=O)Me and —OC(=O)Et,
$C_{1-7}$alkylsulfonate is selected from —SO$_3$Me or —SO$_3$Et,
short chain alkyl group is $CH_2CH=C(CH_3)_2$,
wherein, if the compound is a compound of formula II, then:
$R^{1A}$ is: —OMe, —OC(=O)Me, —COOMe, —SO$_3$H, —SO$_3$M, or —SO$_3$Me.

15. A method as claimed in claim 14 wherein each of $R^{1A}$, $R^{2A}$, and $R^{1B}$ and $R^{2B}$ if present,
unsubstituted $C_{1-7}$-alkyl -Me,
$C_{1-7}$-alkoxy —OMe,
acyloxy is —OC(=O)Me, and
$C_{1-7}$alkylsulfonate is —SO$_3$Me,
short chain alkyl group is $CH_2CH=C(CH_3)_2$,
wherein, if the compound is a compound of formula II, then:
$R^{1A}$ is: —OMe, —OC(=O)Me, —COOMe, —SO$_3$H, —SO$_{M, or —SO3}$Me.

16. A method as claimed in claim 1 wherein each of $R^3$, $R^4$, $R^5$, and $R^6$ is independently: —H, —OH, -Me, -Et, —OMe, —OEt, —OC(=O)Me, or —OC(=O)Et.

17. A method as claimed in claim 1 wherein each of $R^3$, $R^4$, $R^5$, and $R^6$ is independently: —H, —OH, -Me, —OMe, or —OC(=O)Me.

18. A method as claimed in claim 17 wherein each of $R^3$, $R^4$, $R^5$, and $R^6$ is independently: —H or —OH.

19. A method as claimed in claim 18 wherein each of $R^4$, $R^5$, and $R^6$ is —H.

20. A method as claimed in claim 1 wherein $R^3$ is —H.

21. A method as claimed in claim 1 wherein $R^3$ is —OH.

22. A method as claimed in claim 8 wherein $R^{1A}$ is —SO$_3$H or —SO$_3$M, and each of $R^{2A}$, $R^3$, $R^4$, $R^5$, and $R^6$ is —H.

23. A method as claimed in claim 8 wherein $R^{1A}$ is —OMe, and each of $R^{2A}$, $R^3$, $R^4$, $R^5$, and $R^6$ is —H.

24. A method as claimed in claim 8 wherein $R^{1A}$ is —COOH; each $R^{2A}$, $R^3$, $R^4$, $R^5$, $R^6$ is —H; and $R^7$ $R^8$ are —OH.

25. A method as claimed in claim 8, wherein $R^{1a}$ is methyl; each of $R^{2A}$, $R^3$, $R^4$, $R^5$, $R^6$ is —H; and $R^7$ and $R^8$ are —C(=O)Me.

26. A method as claimed in claim 8, wherein $R^{1A}$ is methyl; each of $R^{2A}$, $R^3$, $R^4$, $R^4$, $R^5$, $R^6$, is —H; and $R^7$ and $R^8$ are both either —SO$_3$H or —SO$_3$M.

27. A method as claimed in claim 8, wherein $R^{1A}$ and $R^{2A}$ are methyl; each of $R^3$, $R^4$, $R^5$, $R^6$ is —H; and $R^7$ and $R^8$ are —C(=O)Me.

28. A method as claimed in claim 1 wherein M is selected from the group consisting of: Na$^+$ and K$^+$.

29. The method of claim 1, wherein the compound is selected from the following compounds and pharmaceutically acceptable salts thereof:

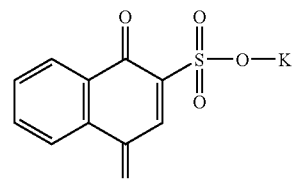
DH8

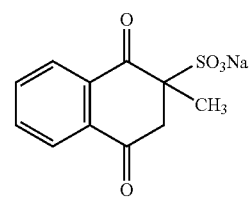
DH3

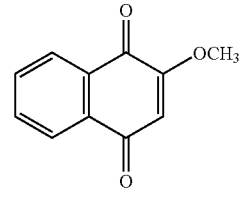
DH17

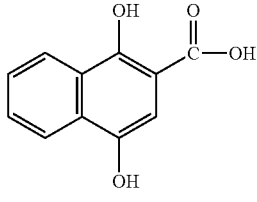
DH5

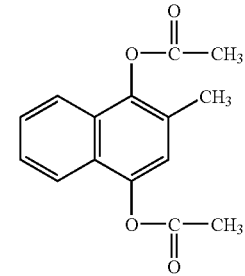
DH9

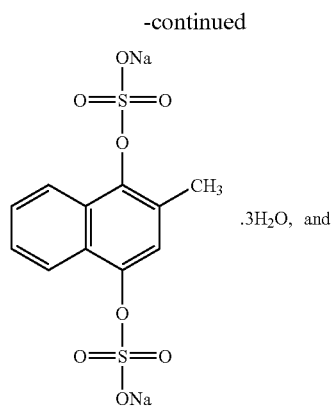
.3H₂O, and
DH13
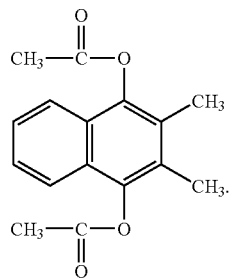
DH11
\* \* \* \* \*

UNITED STATES PATENT AND TRADEMARK OFFICE
CERTIFICATE OF CORRECTION

| | | |
|---|---|---|
| PATENT NO. | : 7,605,179 B2 | Page 1 of 1 |
| APPLICATION NO. | : 10/483266 | |
| DATED | : October 20, 2009 | |
| INVENTOR(S) | : Wischik et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 642 days Delete the phrase "by 642 days" and insert -- by 1244 days --

Signed and Sealed this

Eighteenth Day of May, 2010

David J. Kappos
*Director of the United States Patent and Trademark Office*